(12) United States Patent
Anand et al.

(10) Patent No.: US 10,953,400 B2
(45) Date of Patent: Mar. 23, 2021

(54) HIGH-THROUGHPUT SELECTIVE CAPTURE OF BIOLOGICAL CELLS BY DIELECTROPHORESIS AT A BIPOLAR ELECTRODE ARRAY

(71) Applicant: Iowa State University Research Foundation, Inc., Ames, IA (US)

(72) Inventors: Robbyn K. Anand, Ames, IA (US); Min Li, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 613 days.

(21) Appl. No.: 15/793,587

(22) Filed: Oct. 25, 2017

(65) Prior Publication Data
US 2018/0111124 A1  Apr. 26, 2018

Related U.S. Application Data

(60) Provisional application No. 62/413,157, filed on Oct. 26, 2016.

(51) Int. Cl.
| | |
|---|---|
| B01L 3/00 | (2006.01) |
| B03C 5/00 | (2006.01) |
| C12M 1/00 | (2006.01) |
| G01N 15/02 | (2006.01) |
| G01N 15/14 | (2006.01) |
| B03C 5/02 | (2006.01) |

(52) U.S. Cl.
CPC ..... *B01L 3/502761* (2013.01); *B01L 3/50273* (2013.01); *B01L 3/502746* (2013.01); *B01L 3/502769* (2013.01); *B03C 5/005* (2013.01); *B03C 5/026* (2013.01); *C12M 47/04* (2013.01); *B01L 2200/0652* (2013.01); *B01L 2200/0668* (2013.01); *B01L 2300/0645* (2013.01); *B01L 2400/0424* (2013.01); *B03C 2201/26* (2013.01); *G01N 15/0266* (2013.01); *G01N 15/1484* (2013.01); *G01N 2015/149* (2013.01)

(58) Field of Classification Search
CPC ....... B01L 3/502761; B01L 2200/0668; B01L 2200/0652; C12M 47/04; G01N 2015/149
See application file for complete search history.

(56) References Cited

U.S. PATENT DOCUMENTS

2016/0199853 A1   7/2016  Harwood et al.

OTHER PUBLICATIONS

Qin, Xi. "Separation of Circulating Tumor Cells Using Resettable Cell Traps." Thesis 2015. (Year: 2015).*
Gascoyne, Peter R. C. et al. "Dielectrophoretic separation of mammalian cells studied by computerized image analysis." Measurement Science and Technology (1992) 439-445. (Year: 2015).*
(Continued)

*Primary Examiner* — Christopher Adam Hixson
(74) *Attorney, Agent, or Firm* — McKee, Voorhees & Sease, PLC

(57) ABSTRACT

A microfluidic device comprising one or more fluidic microchannels and one or more arrays of wireless bipolar electrodes is disclosed. The disclosed microfluidic device can be used to separate cells, especially rare cells, from its biological matrix. The disclosed device can isolate cells in a high-throughput fashion and without any modification or labelling to the cells. Cells isolated using the disclosed devices does not lose their vitality.

29 Claims, 15 Drawing Sheets
(10 of 15 Drawing Sheet(s) Filed in Color)

(56) References Cited

OTHER PUBLICATIONS

Dharmasiri, Udara et al., "High-Throughput Selection, Enumeration, Electrokinetic Manipulation, and Molecular Profiling of Low-Abundance Circulating Tumor Cells Using a Microfluidic System", Analytical Chemistry, 2011, 83, pp. 2301-2309. Feb. 14, 2011.
Alazzam, Anas et al., "Interdigitated comb-like electrodes for continuous separation of malignant cells from blood using dielectrophoresis", Electrophoresis Journal, 2011, 32, pp. 1327-1336. Jan. 8, 2011.
Gascoyne, Peter et al., "Isolation of rare cells from cell mixtures by dielectrophoresis", Electrophoresis Journal, 2009, 30, pp. 1388-1398. Oct. 23, 2008.
Henslee, Erin et al., "Selective Concentration of Human Cancer Cells Using Contactless Dielectrophoresis", Electrophoresis Journal, 2011, 32, pp. 2523-2529. May 2, 2011.
Chow, Kowk-Fan et al., "A Large-Scale, Wireless Electrochemical Bipolar Electrode Microarray", American Chemical Society, 2009, 131, pp. 8364-8365. Apr. 3, 2009.
Anand, Robbyn K., et aL, "Negative Dielectrophoretic Capture and Repulsion of Single Cells at a Bipolar Electrode: The Impact of Faradaic Ion Enrichment and Depletion", Journal of the American Chemical Society, 2015, 137, pp. 776-783. Jan. 6, 2015.
Chang, Byoung-Yong, et al., "Two-Channel Microelectrochemical Bipolar Electrode Sensor Array", Analyst, 2012, 137, pp. 2827-2833. Apr. 25, 2012.
Guerrette, Joshua P. et al., "Fluorescence Coupling for Direct Imaging of Electrocatalytic Heterogeneity", Journal of the American Chemical Society, 2013, 135, pp. 855-861. Dec. 17, 2012.
Li, Min et aL, "High-Throughput Selective Capture of Single Circulating Tumor Cells by Dielectrophoresis at a Wireless Electrode Array", Journal of the American Chemical Society, pp. A-J. Jun. 13, 2017.
Qiao, Wen et al., "Wirelssly Powered Microfluidic Dielectrophoresis Devices Using Printable RF Circuits", The Royal Society of Chemistry, 2011, 11, pp. 1074-1080. Jan. 4, 2011.
Cemazar, Jaka et aL, "Enhanced Contactless Dielectrophoresis Enrichment and Isolation Platform via Cell-Scale Microstructures", American Institute of Physics, 10, 014109, 2016.
Li, Min et al, "High-Throughput Selective DEP Capture and On-Chip Analysis of Single CTCs". GRC poster 2017.
Antfolk, Maria et al., "Label-Free Single-Cell Separation and Imaging of Cancer Cells Using an Integrated Microfluidic System", Scientific Reports, vol. 7, pp. 1-12. Apr. 20, 2017.
Cohen, Dawn E. et al., "Self-Digitization of Sample Volumes", Analytical Chemistry, vol. 82, No. 13, pp. 5707-5717. Jul. 1, 2010.
Gansen, Alexander et al., "Digital Lamp in a Sample Self-Digitization (SD) Chip", Lab Chip, vol. 12, pp. 2247-2254. Feb. 8, 2012.
Kim, Soo Hyeon et al., "Efficient Analysis of a Small Number of Cancer Cells at the Single-Cell Level Using an Electroactive Double-Well Array", Lab Chip, vol. 16, pp. 2440-2449. May 4, 2016.
Kim, Soo Hyeon et al., "Quantifying Genetically Inserted Fluorescent Protein in Single iPS Cells to Monitor Nanog Expression Using Electroactive Microchamber Arrays", Lab Chip, vol. 14, pp. 730-736. 2014.
Kobayashi, Marina et al., "Cancer Cell Analyses at the Single Cell-Level Using Electroactive Microwell Array Device", PLOS ONE, vol. 10, pp. 1-10. Nov. 11, 2015.
Schneider, Thomas et al., "Self-Digitization of Samples into a High-Density Microfluidic Bottom-Well Array", Analytical Chemistry, vol. 85, pp. 10417-10423. 2013,
Thompson, Alison M. et al., "Self-Digitization Mcirofluidic Chip for Absolute Quantification of mRNA in Single Cells", Analytical Chemistry, vol. 86, pp. 12308-12314. 2014.

* cited by examiner

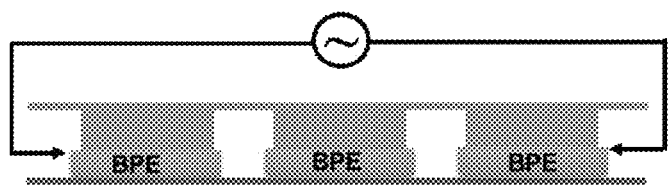
*FIG. 2A*
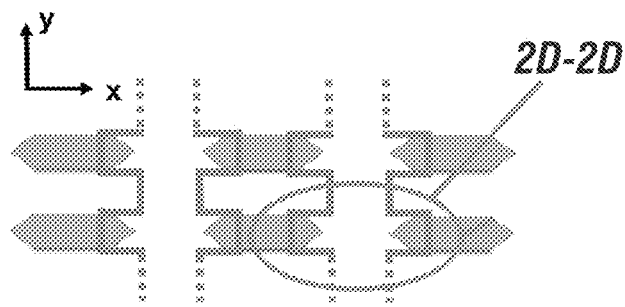
*FIG. 2B*
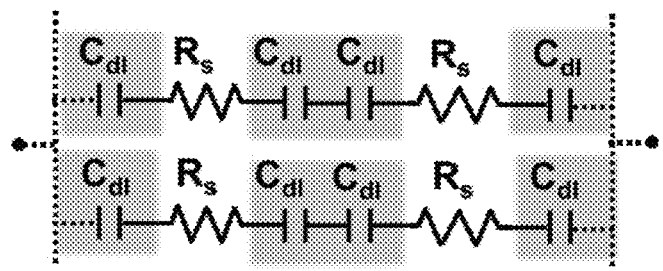
*FIG. 2C*
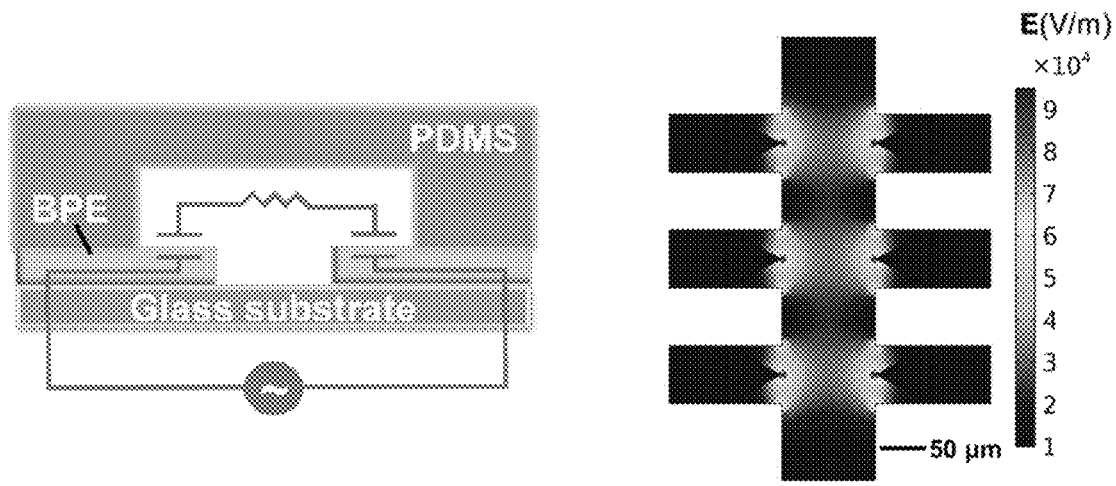
*FIG. 2D*
*FIG. 2E*

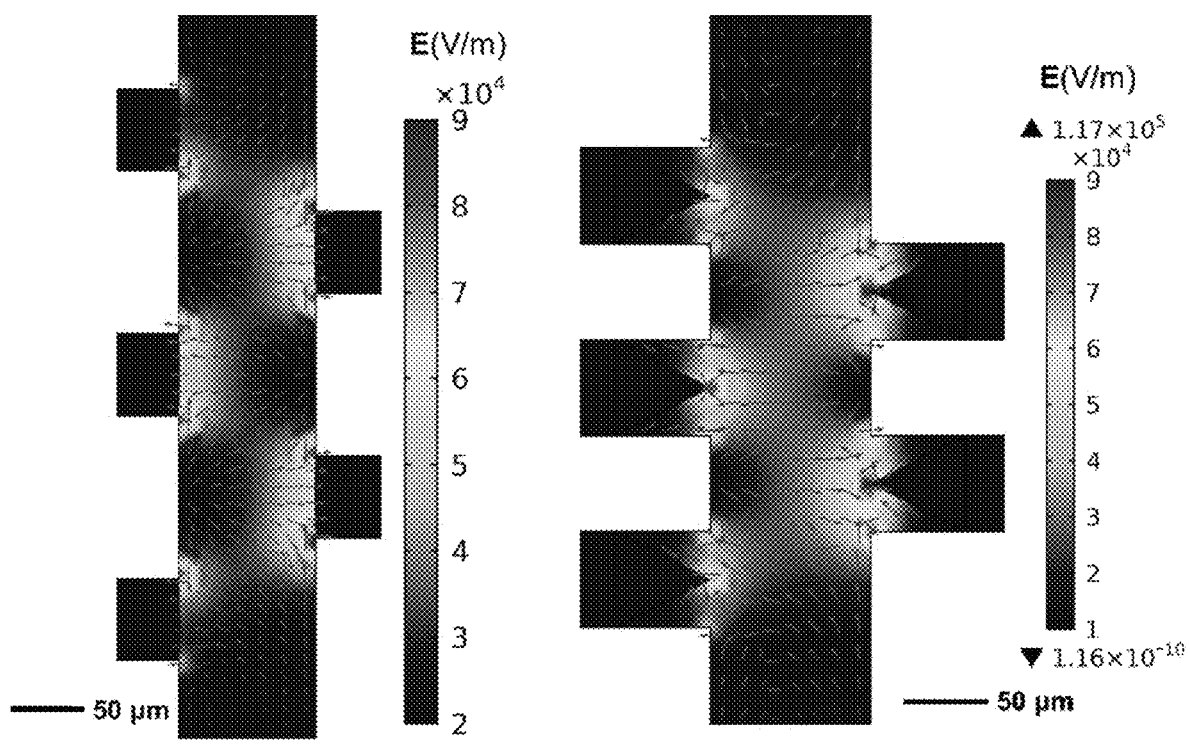
*FIG. 5A*  *FIG. 5B*

HIGH-THROUGHPUT SELECTIVE CAPTURE OF BIOLOGICAL CELLS BY DIELECTROPHORESIS AT A BIPOLAR ELECTRODE ARRAY

CROSS-REFERENCE TO RELATED APPLICATIONS

This application claims priority to U.S. Provisional Application Ser. No. 62/413,157, filed Oct. 26, 2016, titled "HIGH-THROUGHPUT SELECTIVE CAPTURE OF BIOLOGICAL CELLS BY DIELECTROPHORESIS AT A BIPOLAR ELECTRODE ARRAY", which is herein incorporated by reference in its entirety.

FIELD OF THE INVENTION

The present invention is related to a high-throughput microfluidic device and method for capturing cells by their dielectric properties at a wireless bipolar electrode array. Specifically, a microfluidic device that comprises one or more arrays of wireless bipolar electrodes is disclosed. Such a microfluidic device is capable of capturing a few rare cells from a biological matrix, such as blood, in a high-throughput fashion.

BACKGROUND OF THE INVENTION

Differentiating or separating a few cells from a matrix or mixture containing multiple cell types is a challenging and exciting task that is in high demand. For example, the need to study circulating tumor cells (CTCs) and the potential impact of isolating CTCs (either single CTC cell or micro-emboli of CTCs) make a compelling argument for the need for new devices and methods capable of rare cell isolation.

CTCs are cells that have detached from the primary tumor and migrated into blood vessels. A fraction of these CTCs seed metastases by extravasation into the parenchyma of foreign tissues for subsequent growth of tumors. Understanding and preventing this process is critical because metastasis leads to 90% of epithelial cancer-related deaths.

Recent years have witnessed growing efforts to study CTCs for the development of effective therapies. For instance, clinical studies have shown that an inverse correlation exists between survival and the number of CTCs. This correlation is independent of the line of therapy. Clinical studies have also shown that the reduction or elimination of CTCs after treatment prolongs survival. These findings indicate that the enumeration of CTCs is relevant for diagnosis, prognosis and evaluation of drug resistance. Additionally, the genetic mutations exhibited in CTCs may provide guidance for the selection of therapies, thus personalizing treatment. For example, metastatic colorectal cancer patients with wild-type KRAS can benefit from anti-epidermal growth factor receptor (EFGR) monoclonal antibody (mAb) treatment, while those with mutated KRAS are not able to use this monotherapy. In this scenario, the study of CTCs including isolation and characterization is of paramount importance for the successful preparation and implementation of anticancer therapies.

Despite CTCs' promise as a clinical indicator and therapeutic target, the separation of CTCs from whole blood, which is the first inevitable step of overall analysis, is challenging. First, CTCs are extremely rare, such that there can be as few as 1 CTC per $10^9$ erythrocytes and $10^7$ leukocytes. In a standard blood volume of 7.5 mL employed, the number of CTCs detected by techniques that are currently clinically available is normally less than 10.

Second, due to the heterogeneous nature of the cell populations found in primary tumors and the changes undergone by these cells during metastatic events, the phenotypic characteristics of CTCs can vary widely. Examples include the nuclear to cytoplasmic ratios (N/C) (The average N/C ratio of CTCs in breast cancer patients is 4.0, while it is 1.43 in prostate cancer patients), deformability (CTCs with large N/C ratio are less deformable and less invasive), size (the size of CTCs reported is over a wide range from 4 μm to 30 μm, even from a single patient) and protein expression. The proteins such as cytokeratin (CK) and epithelial cell adhesion molecules (EpCAM) present on the surface of tumor cells vary tremendously depending on the patient, the type of cancer, and the stage of the tumor.

In spite of these challenges, tremendous progress has been made using one or more of CTCs' unique properties to discriminate or isolate them from surrounding blood cells. The most popular isolation techniques employ immunofluorescent labeling of the epithelial cell adhesion marker (EpCAM) and devices utilizing such techniques. EpCAM is expressed exclusively on the surface of epithelial cells, and it is thus widely applied in antibody-based approaches as a diagnostic marker to distinguish CTCs from peripheral blood cells. For examples, Soper et. al. (Dharmasiri, U.; Njoroge, S. K.; Witek, M. A.; Adebiyi, M. G.; Kamande, J. W.; Hupert, M. L.; Barany, F.; Soper, S. A. Analytical Chemistry 2011, 83, 2301-2309) developed a high-throughput micro-sampling unit (HTMSU) containing anti-EpCAM antibodies immobilized on the walls of selection beds to capture SW620 and HT29 cells (colorectal cancer cell lines) from 1 mL of whole blood in ~40 min. CellSearch (Veridex™, Warren, Pa., USA) utilizes EpCAM-coated ferrofluid nanoparticles to separate CTCs from blood cells.

Despite its reputation as the only FDA cleared clinical testing program, CellSearch, like other EpCAM-based approaches, suffers from its inability to capture CTCs that inherently do not express EpCAM or that have lost this expression during the epithelial-mesenchymal transition (EMT) process. Importantly, the subpopulation of CTCs that have undergone the EMT is most likely to survive and invade, therefore determining disease outcome. Underscoring the shortcomings of these assays is the fact that cultured cancer cells with high expression of EpCAM, such as MCF7 and SW620 cells (MCF7=$5\times10^5$ and SW620=$1\times10^6$ EpCAM molecules/cell), have to be chosen and must be employed for evaluation of the assay to obtain reliable results.

Label-free techniques based on the physical properties of CTCs circumvent reliance on protein expression so that some capture biases may be decreased. For instance, filtration techniques integrate the micro-scale constrictions of weirs, pillars, or pores into cell separation so that cells with desired size and deformability can be retained. Commercially available polycarbonate membranes have been utilized for the isolation of CTCs, and synthetic filters have been developed to improve the capture or release efficiency. Clinical evaluations of these filtration approaches are ongoing. However, the size distribution of CTCs overlaps with that of leukocytes, thus resulting in CTC loss or leukocyte contamination.

As a further concern, clogging within filters and subsequent change in flow rate or velocity may cause shear stress and potential damage or loss of CTCs. In comparison with filtration, hydrodynamic chromatography such as lateral displacement separation and spiral channels impart cells in fluids with different velocity based on size differences and deformability.

Though the throughput is significantly improved (up to 600 mL/h), enrichment becomes poorer due to the inability of these techniques to differentiate nucleated cells. The combination of multiple capture steps (e.g., immunoaffinity labeling and size-based filtration) in a single device such as ensemble-decision aliquot ranking (eDAR) or the On-Q-ity C5 chip (On-Q-ity Inc., Waltham, Mass.) can couple the error incurred in each individual isolation step, thus resulting in cumulative bias.

Physical isolation devices that employ dielectrophoresis (DEP) not only feature antibody-independent separation, but they also integrate size and dielectric properties of CTCs. The variation of dielectric properties due to a cell's composition, morphology, membrane and interior structures results in the cell's unique DEP response. Therefore, a separation based on DEP exhibits less selection bias when compared with those based on size- and antibody-based approaches. For instance, Alazzam et al. (Alazzam, A.; Stiharu, I.; Bhat, R.; Meguerditchian, A. N. Electrophoresis 2011, 32, 1327-1336) applied DEP via interdigitated comb-like electrodes to achieve 96% capture efficiency of MDA-MB-231 cells (an invasive breast cancer cell line) from normal blood cells. Gascoyne et al. (Gascoyne, P. R.; Noshari, J.; Anderson, T. J.; Becker, F. F. Electrophoresis 2009, 30, 1388-1398) reported the application of dielectrophoretic field-flow fractionation (DEP-FFF) to isolate three different kinds of tumor cells with above 90% efficiency from the nucleated cell fraction of a blood sample (the 'buffy coat'). Demonstrating the potential of DEP for a high degree of selectivity, Henslee et al. (Henslee, E. A.; Sano, M. B.; Rojas, A. D.; Schmelz, E. M.; Davalos, R. V. Electrophoresis 2011, 32, 2523-2529) proved that late-stage breast cancer cells could be isolated from early and intermediate-stage CTCs.

DEP is also amenable to downstream analysis of captured cells. For example, an electroactive double-well array was fabricated to achieve single-cell DEP capture of PC3 cells, which was followed by analysis of the intracellular β-galactosidase activity.

However, despite these advantages, when compared to filtration and hydrodynamic chromatography with throughput at the order of 10-100 mL/h, current devices or methods utilizing DEP suffer from relatively low throughput in the range of 0.01 mL/h to 1.0 mL/h (Čemažar, J.; Douglas, T. A.; Schmelz, E. M.; Davalos, R. V. Biomicrofluidics 2016, 10, 014109). Clearly, there is still need for the development of high-throughput DEP devices in this CTCs separation field alone.

Accordingly, it is an objective of the disclosure to provide a high-throughput DEP microfluidic device and method of using it that is readily scalable along both x and y directions via the employment of one or more arrays of wireless bipolar electrodes (BPEs) for separation of rare cells, such as CTCs (either single CTC cell or microemboli of CTCs) from a matrix or mixture comprising many cells. It is also an objective of this disclosure to provide a method for utilizing the claimed high-throughput DEP microfluidic device for separation of a certain type of cells from all other types of cells.

The disclosed microfluidic devices, while retaining the inherent advantages of DEP, including selective and label-free isolation of cells and ease of fabrication, and provide an avenue for some point-of-care applications.

Other objects, advantages and features of the present invention will become apparent from the following specification taken in conjunction with the accompanying examples or drawings.

BRIEF SUMMARY OF THE INVENTION

In one aspect, the present disclosure provides a microfluidic device, the device comprises one or more fluidic microchannels that are configured to retain and move an ionically conductive solution; and one or more arrays of wireless bipolar electrodes, wherein each array of wireless bipolar electrodes comprises two or more bipolar electrodes; and wherein the one or more arrays are placed along the one or more fluidic microchannels.

In another aspect, the present disclosure provides a high-throughput cell isolation system, the system comprises the disclosed microfluidic device herein and an ionically conductive solution.

In another aspect, the present disclosure provides a method for isolation of a cell from a biological matrix. The method comprises contacting a biological sample with an ionically conductive solution in a fluidic device comprising one or more wireless bipolar electrodes and applying an AC electric field to the ionically conductive solution for a period time such that a targeted cell is trapped at the tip of the bipolar electrode or aggregated at a point where the electric field is a local maximum; wherein the biological sample contains a targeted cell to be isolated.

In yet another aspect, the present disclosure provides a method of isolating a cell, especially a rare cell, from a biological matrix, the method comprises contacting a biological sample with an ionically conductive solution in any of the microfluidic devices disclosed herein, and applying an AC electric field to the ionically conductive solution and the wireless bipolar electrodes for a period of time, so a targeted cell is trapped at the tip of the bipolar electrode or aggregated at a point where the electric field is a local maximum; wherein the biological sample contains the targeted cell to be isolated.

A major benefit of the current disclosure is that the removal of the requirement for wire leads opens up design options that would be difficult or impossible otherwise.

The advantage of the microfluidic devices disclosed herein is that it is capable to process a biologic sample in a high throughput fashion, from about 0.01 mL/h to about 30.0 mL/h, so that a rare type of cells, single cells or microemboli of cells can be isolated from the complex matrix, without any labeling or modification to the cells and without losing any vitality of the cells. The captured cells can be isolated, accumulated, and then used for its characterizations, such as its invasiveness and response to various drugs. The microfluidic devices disclosed herein have potential clinic applications, such as for accurate and early cancer diagnosis and selection of its effective treatment.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows an illustration of a cross-sectional view of the setup of BPEs in an AC electric field.

FIG. 2B shows an illustration of an extension scheme of the microchannels along x- and y-direction using BPEs and one example of the adjustment of electric field intensity by the design of BPEs.

FIG. 2C depicts the equivalent circuit for the parallel-channel design.

FIG. 2D depicts the location of double layer capacitance at each BPE tip.

FIG. 2E shows a 2D simulation of the electric field distribution across a single microchannel flanked by 6 BPE tips.

FIG. 5A shows the electric field simulation in an array-based design using square BPE.

FIG. 5B shows the electric field simulation in an array-based design using triangle BPE.

DETAILED DESCRIPTION OF THE INVENTION

Figure 1:
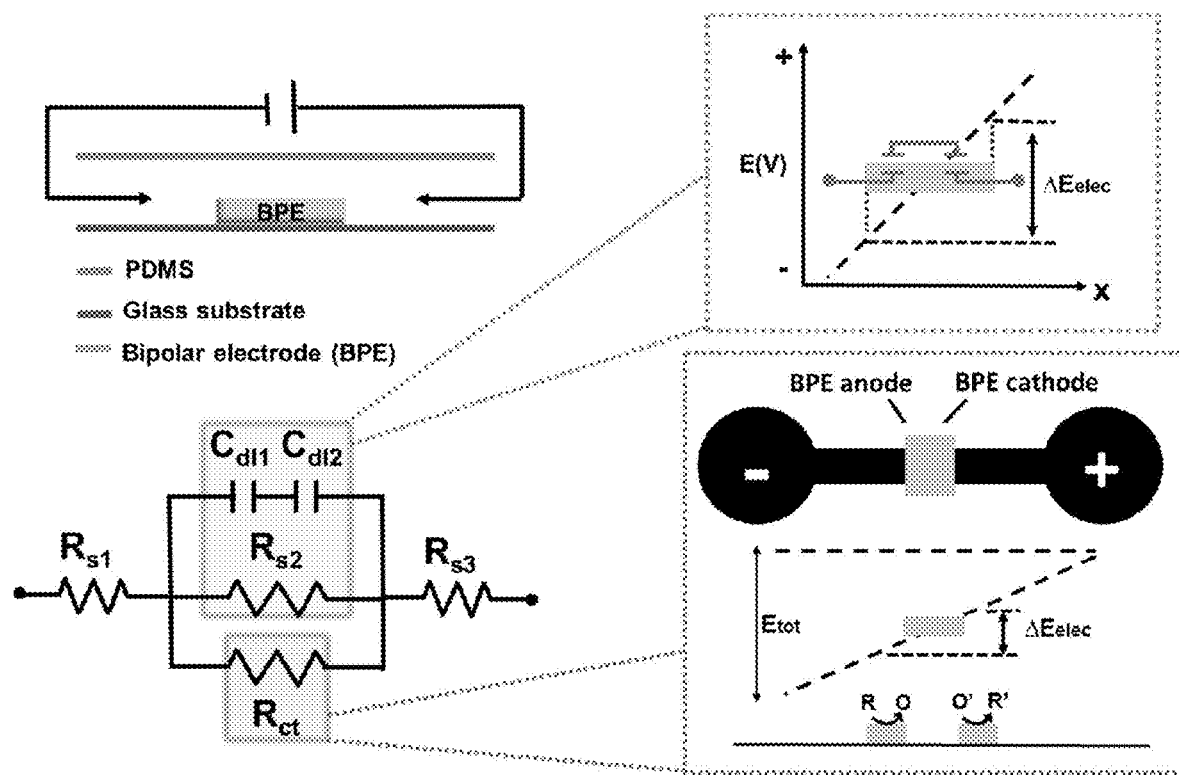
FIG. 1 shows an illustration of the functions of BPEs in a DC electric field. The setup of BPE in a microfluidic device (top left); Equivalent circuit obtained in the design (bottom left); Scheme of the formation of the double layer capacitance (top right); Illustration of the faradaic reactions that could occur at the BPEs if a DC electric field were applied such that a sufficiently high overpotential became available to drive oxidation and reduction reactions at opposite ends of the BPEs (bottom right). By applying an AC electric field, faradaic reactions are avoided.

The present disclosure relates to a high-throughput microfluidic device comprising one or more wireless bipolar electrode arrays, to separate one type of cells from all other types of cells. The embodiments of this invention are not limited to any particular device, which can vary and are understood by skilled artisans based on the present disclosure herein. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. The preferred materials and methods are described herein. In describing and claiming the embodiments of the present invention, the following terminology will be used in accordance with the definitions set out below.

The term "about," as used herein, refers to variations in size, distance or any other types of measurements that can be resulted from inherent heterogeneous nature of the measured objects and imprecise nature of the measurements itself. The term "about" also encompasses variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods, and the like. The term "about" also encompasses amounts that differ due to different equilibrium conditions for a composition resulting from a particular initial mixture. Whether or not modified by the term "about", the claims include equivalents to the quantities.

The present disclosure provides a microfluidic device comprising one or more arrays of wireless bipolar electrodes. A bipolar electrode (BPE) is a conductor that, when exposed to an external electrical field, can facilitate oxidation and reduction reactions simultaneously at its opposite ends. For example, a BPE can comprise a strip of metal embedded in a microfluidic channel filled with an aqueous electrolyte. When a DC electric potential is applied across the reservoirs of the microchannel, a linear potential drop is expected along the channel length due to its high electrical resistance. This linear electric field leads to potential differences between the BPE (an equipotential object) and the solution in contact with its ends. An electrical double layer forms at each end of the BPE, and faradaic reactions occur if the potential differences at the BPE/solution interface (cathode and anode) provide sufficient overpotential to drive simultaneously the reduction and oxidation of available redox species as illustrated in FIG. 1.

FIG. 1 shows an illustration of the functions of BPEs in a DC electric field. The setup of BPE in a microfluidic device is shown at top left and its equivalent circuit that describes this system is shown at bottom left. The scheme of the formation of the double layer capacitance is shown at top right. Illustration of the faradaic reactions that could occur at the BPEs if a DC electric field were applied such that a sufficiently high overpotential became available to drive oxidation and reduction reactions at opposite ends of the BPE is shown at bottom right. By applying an AC electric field only, faradaic reactions are avoided.

In this microchannel, a current flows between the driving electrodes either via ionic conduction in solution or through the BPE via capacitive charging or charge transfer (faradaic reactions). The solution resistance (to ionic current) is represented by $R_{s1}$ (left of BPE), $R_{s2}$ (above BPE), and $R_{s3}$ (right of BPE). $R_{ct}$ is the resistance to charge transfer reactions, whereas $C_{dl1}$ and $C_{dl2}$ are the double layer capacitance at each end of the BPE. The key feature of this configuration is to achieve faradaic reactions (current through Rct) without direct ohmic electric contact to the BPEs. For example, Crooks and coworkers designed a BPE array composed of 1000 individual BPEs to facilitate faradaic reactions (Chow, K. F.; Mavre, F.; Crooks, J. A.; Chang, B. Y.; Crooks, R. M. J Am. Chem. Soc. 2009, 131, 8364-8365). They employed electrogenerated chemiluminescence (ECL) at the anode to report the activation of a sensing event leading to a reduction reaction at the cathode. The ECL intensity profile indicated a uniform response from each BPE under the applied DC electric field. A wide range of applications hitherto bears testimony to the fact that BPEs are effective, convenient, and robust for the detection, sensing, separation and enrichment of a wide variety of analytes.

However, when a sufficiently high frequency AC field is applied rather than a DC electric field, faradaic reactions do not occur (Ret approaches infinity when the field frequency is greater than the rate of electron transfer from available redox species). Further, if the top of the microchannel meets the BPE, then the possibility of ionic current above the BPE is removed ($R_{s2}$ becomes infinite). In this scenario, the continuous charging and discharging of the electrical double layer formed between each end of a BPE and the solution becomes the primary route by which the electric field drives current between the driving electrodes.

Due to this capacitive charging, separate parallel microchannels can remain electrically interconnected by the embedded BPEs in an AC electric field. FIG. 2A shows an illustration of a cross-sectional view of the setup of BPEs in an AC electric field. FIG. 2B shows an illustration of an extension scheme of the microchannels along x- and y-direction using BPEs and one example of the adjustment of electric field intensity by the design of BPEs. FIG. 2C depicts the equivalent circuit while FIG. 2D depicts the location of double layer capacitance at each BPE tip. FIG. 2E shows a 2D simulation of the electric field distribution across a single microchannel flanked by 6 BPE tips. Due to the equipotential quality of conductors, each BPE takes on a potential that is intermediate to the potential of the solution at its ends, and then a drop in potential (electric field) is distributed across the solution in each microchannel. This electric field distribution can be readily tuned by the dimensions of the BPEs. For instance, pointed BPEs result in a maximum electric field at the BPE tip, while minimum field intensity is located at the middle of the channels as shown in FIG. 2E. In this way, the BPEs not only transmit the AC electric field across the chip but also shape the electric field in a desired way.

DEP is a field-induced force acting on a polarizable particle when exposed to a non-uniform electric field. The external electric field (E) induces the surface charges (bound and free charges) that accumulate at the particle interface. The gradient in the electric field exerts differential force on the two opposing ends of the resulting induced electrical dipole, resulting in a net dielectrophoretic force. The time-averaged DEP force experienced by a homogeneous spherical particle with radius r in a medium of permittivity $\varepsilon^*_m$ is given by equation (1):

$$(F\_DEP) = 2\pi r^3 \varepsilon_m \text{Re}[K(\omega)] \nabla |E|^2 \quad (1)$$

Where $\text{Re}[K(\omega)]$ is the real part of Clausius-Mossotti factor $$K(\omega) = (\varepsilon^*_p - \varepsilon^*_m)/(\varepsilon^*_p + 2\varepsilon^*_m) \quad (2)$$

which determines the direction and relative strength of DEP force as a function of applied field frequency. Here, $\varepsilon^*_p$ and $\varepsilon^*_m$ are the frequency dependent complex permittivity of the particle and medium, respectively. When $[K(\omega)]$ is positive, the induced DEP force, known as positive DEP (pDEP) displaces particles toward higher electric field, while particles move toward lower electric field when $[K(\omega)]$ is negative, termed as negative DEP (nDEP). Importantly, the unique frequency-dependent polarization responses of biological cells allow them to be separated by DEP at a field frequency and medium conductivity where significantly disparate values of $[K(\omega)]$ can be achieved for each kind of cell.

For example, MDA-MB-231 (breast cancer) cells experienced pDEP in the range of 45-85 kHz in a medium with conductivity of 30 mS/m (milli-Siemen per meter, wherein a Siemen is the inverse of Ohms. $1 S=1 O^{-1}$). The frequency above which cells transition from an nDEP to pDEP response, the cross-over frequency (cof), is 110-190 kHz for Jurkat E6-1 T cells (a model white blood cell line) in a medium with a conductivity of 40 mS/m. A decrease in medium conductivity will result in a decrease in the cof.

In one aspect, the present disclosure provides a microfluidic device. The device comprises one or more fluidic microchannels that are configured to retain and move an ionically conductive solution, and one or more arrays of wireless bipolar electrodes, wherein each array of wireless bipolar electrodes comprises two or more bipolar electrodes, and the one or more arrays are placed along or inside the one or more fluidic microchannels.

As used herein, a microchannel is referred to as a passageway with a cross section of from a few micrometers (several $10^{-6}$ meters) to about a few hundred micrometers (hundreds $10^{-6}$ meters) and with a length of from a few hundred micrometers (hundreds $10^{-6}$ meters) to about a few millimeters (several or tens $10^{-3}$ meters). The cross section of a microchannel in principle can have any two-dimensional shape, such as square, rectangular, circle, or a combination thereof. A microchannel may be straight or curved. In some embodiments, a microchannel may be encircled by a wall or several walls or by a complete circular wall, except two openings at both ends. In some embodiments, a microchannel does not have its top wall or sidewalls.

In some embodiments, the wall(s) or some parts of the wall of a microchannel is a part of the wireless bipolar electrodes or other conductive or nonconductive parts of the microfluidic device. In some embodiments, the wall(s) or some parts of the wall of a microchannel comprises polymeric material, conductive, non-conductive, semi-conductive material, or a combination thereof.

In some other embodiments, the microfluidic devices disclosed herein have 1, 2, 4, 8, 16, 32, 64, or much more microchannels. A number of microchannels can be grouped together and then connected fluidly with another group(s) of microchannels. Two or more microchannels are grouped together by fluidly connecting their ends. Within each group of microchannels, any two microchannels can be parallel to each other, on top of each other, or in another arrangement.

In some embodiments, one or more microchannels are the same. In some other embodiments, one microchannel can be different from other microchannels in the same microfluidic devices.

In some embodiments, a few microchannels can merge into a bigger channel or reservoir for design or throughput purposes to form a merged microchannel or reservoir. As the result of merging, a merged microchannel or reservoir has the combined size or footprint of the microchannels that are merged. In this situation, the walls or barriers between merged microchannels are dismantled or removed.

As used herein, the width of a microchannel is referred to as the horizontal distance of the two points that are on the opposite edges of the cross section along the intended fluidic flow and are furthest away from each other. As used herein, the depth of a microchannel is referred to as the vertical distance of the points that one of the opposite edges of the cross section along the intended fluidic flow and are furthest away from each other. As used herein, the length of a microchannel is the distance between the two ends along the intended fluid flow. The length of a microchannel is usually the length of its longest dimension. The two shorter dimensions usually defines the cross section described above.

In some embodiments, within each microchannel of the disclosed microfluidic device, there are one or more arrays of wireless bipolar electrodes along the wall(s) of the microchannels. The arrays of wireless bipolar electrodes can be on the bottom/floor wall(s), side wall(s), or top walls of the microchannel.

As used herein, a wireless bipolar electrode is referred to as a piece of conductive or semi-conductive material comprising two ends as one skilled in the art would understand. A wireless bipolar electrode as used herein has dimensions within from about a few micrometers to about a few millimeters. A wireless bipolar electrode used in this disclosure does not require a lead or ohmic connection to a power source.

As used herein, an array of wireless bipolar electrodes (BPEs) refers to a group of at least two or more wireless bipolar electrodes. And within the group any one of the wireless bipolar electrodes is connected via an ionically conductive medium with at least one other wireless bipolar electrode. Two or more arrays of wireless BPEs can be connected with each other electronically or conductively through the ends of each array.

In some embodiments, a wireless BPE is parallel to the other wireless BPEs in the same array. In some embodiments, a wireless BPE is aligned with another wireless BPE in a different array of wireless BPEs within the same microchannel, merged microchannel, or reservoir formed by the merged microchannels. In some other embodiments, an array of wireless BPEs are staggered with another array of wireless BPEs within the same microchannel, merged microchannel, or reservoir formed by the merged microchannels.

As used herein, a microchamber or micropocket is referred to as a micro scale space at least partially enclosed by the materials of other components of the microfluidic devices or by its own wall(s). As used herein, the term "microchamber" and "micropocket" are used interchangeably. In some embodiments, a microchamber hosts one end of a wireless BPE and has an opening to a microchannel, merged microchannel, or reservoir formed by the merged microchannels. In some embodiments, a microchamber has a dimension of from about a few micrometers to about a few hundred micrometers of its width, height, and depth.

As used herein, the width of a microchamber is referred to the horizontal distance of the two points that are on the opposite edges of the cross section on the wall of the microchannel and are furthest away from each other. As used herein, the height or tallness of a microchamber is referred to the vertical distance of the points that are on the opposite edges of the cross section on the wall of the microchannel and are furthest away from each other. As used herein, the depth of a microchamber is the shortest distance from the edge of the fluid flow to the bottom of the microchamber.

In some embodiments, all microchambers are the same. In some other embodiments, one or some of the microchambers in a disclosed microfluidic device can be different from other microchambers in the same microfluidic device.

In some embodiments, a microchamber is inside a wall of the microchannels, merged microchannels, or reservoir formed by the merged microchannels.

A microchamber can have any shape as one skilled in the art can understand. In some embodiments, a cross section of a microchamber is a square, rectangle, circle, or a combination thereof. In some embodiments, a microchamber does not have one or two of its top wall(s), floor wall(s), or side walls.

In some embodiments, the power source is not in direct contact with the wireless bipolar electrodes.

In some other embodiments, the one or more fluidic microchannels have a width of from about 10 μm to about 200 μm, from about 5 μm to about 200 μm, from about 1 μm to about 200 μm, from about 10 μm to about 20 μm, from about 10 μm to about 30 μm, from about 10 μm to about 40 μm, from about 10 μm to about 50 μm, from about 10 μm to about 60 μm, from about 10 μm to about 70 μm, from about 10 μm to about 80 μm, from about 10 μm to about 90 μm, from about 10 μm to about 100 μm, from about 10 μm to about 120 μm, from about 10 μm to about 140 μm, from about 10 μm to about 160 μm, from about 10 μm to about 180 μm, or from about 1, 2, 5, 10, 15, or 20 μm to any value between 25 μm and 200 μm. In some other embodiments, the width of the one or more fluidic microchannels is about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, or about any value there between.

In some other embodiments, the one or more fluidic microchannels have a depth of from about 10 μm to about 100 μm, from about 5 μm to about 100 μm, from about 10 μm to about 15 μm, from about 10 μm to about 20 μm, from about 10 μm to about 25 μm, from about 10 μm to about 30 μm, from about 10 μm to about 35 μm, from about 10 μm to about 40 μm, from about 10 μm to about 45 μm, from about 10 μm to about 50 μm, from about 10 μm to about 55 μm, from about 10 μm to about 60 μm, from about 10 μm to about 70 μm, from about 10 μm to about 80 μm, from about 10 μm to about 90 μm, from about 15 μm to about 20 μm, from about 15 μm to about 25 μm, from about 15 μm to about 30 μm, from about 15 μm to about 35 μm, from about 15 μm to about 40 μm, from about 15 μm to about 45 μm, from about 15 μm to about 50 μm, from about 15 μm to about 60 μm, from about 15 μm to about 70 μm, from about 15 μm to about 80 μm, from about 15 μm to about 90 μm, from about 15 μm to about 100 μm, from about 20 μm to about 50 μm, from about 20 μm to about 60 μm, from about 20 μm to about 70 μm, from about 20 μm to about 30 μm, from about 20 μm to about 35 μm, from about 20 μm to about 40 μm, from about 20 μm to about 45 μm, about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 100 μm, or about any values there between.

In some embodiments, wherein the one or more fluidic microchannels have a length of from about 0.1 mm to about 10 mm, from about 0.1 mm to about 0.5 mm, from about 0.1 mm to about 1 mm, from about 0.1 mm to about 2 mm, from about 0.1 mm to about 3 mm, from about 0.1 mm to about 4 mm, from about 0.1 mm to about 5 mm, from about 0.1 mm to about 6 mm, from about 0.1 mm to about 7 mm, from about 0.1 mm to about 8 mm, from about 0.1 mm to about 9 mm, from about 0.5 mm to about 1 mm, from about 0.5 mm to about 2 mm, from about 0.5 mm to about 3 mm, from about 0.5 mm to about 4 mm, from about 0.5 mm to about 5 mm, from about 0.5 mm to about 6 mm, from about 0.5 mm to about 7 mm, from about 0.5 mm to about 8 mm, from about 0.5 mm to about 9 mm, from about 0.5 mm to about 10 mm, from about 1 mm to about 2 mm, from about 1 mm to about 3 mm, from about 1 mm to about 4 mm, from about 1 mm to about 5 mm, from about 1 mm to about 6 mm, from about 1 mm to about 7 mm, from about 1 mm to about 8 mm, from about 1 mm to about 9 mm, from about 1 mm to about 10 mm, from about 2 mm to about 3 mm, from about 2 mm to about 4 mm, from about 2 mm to about 5 mm, from about 2 mm to about 6 mm, from about 2 mm to about 7 mm, from about 2 mm to about 8 mm, from about 2 mm to about 9 mm, from about 2 mm to about 10 mm, about 0.1 mm, about 0.2 mm, about 0.3 mm, about 0.4, about 0.5 mm, about 0.6 mm, about 0.7 mm, about 0.8 mm, about 0.9 mm, about 1 mm, about 1.5 mm, about 2.0 mm, about 2.5 mm, about 3.0 mm, about 3.5 mm, about 4.0 mm, about 4.5 mm, about 5.0 mm, about 5.5 mm, about 6.5 mm, about 7.5 mm, about 8.0 mm, about 8.5 mm, about 9.0 mm, about 10 mm, or any value there between.

In some embodiments, the distance between adjacent microchannels is from about 10 μm to about 500 μm, from about 25 μm to about 500 μm, from about 0.05 mm to about 0.5 mm, from about 0.05 mm to about 0.1 mm, from about 0.05 mm to about 0.15 mm, from about 0.05 mm to about 0.2 mm, from about 0.05 mm to about 0.25 mm, from about 0.05 to about 0.3 mm, from about 0.05 mm to about 0.35 mm, from about 0.05 mm to about 0.4 mm, from about 0.05 mm to about 0.5 mm, from about 0.1 to about 0.15 mm, from about 0.1 mm to about 0.2 mm, from about 0.1 mm to about 0.25 mm, from about 0.1 to about 0.3 mm, from about 0.1 mm to about 0.35 mm, from about 0.1 mm to about 0.4 mm, from about 0.1 mm to about 0.5 mm, about 0.05 mm, about 0.1 mm, about 0.15 mm, about 0.2 mm, about 0.25 mm, about 0.3 mm, about 0.35 mm, about 0.4 mm, about 0.5 mm, or any value there between.

In some embodiments, the one or more fluidic microchannels have two or more side walls, one or more bottom walls, one or more floor walls, one or more top walls, one or more circular walls, or a combination thereof.

In some embodiments, the one or more arrays of wireless bipolar electrodes are placed along one or more walls of the one or more fluidic microchannels. In some other embodiments, the one or more arrays of wireless bipolar electrodes are placed along the bottom or floor wall(s) of the one or more fluidic microchannels. In some other embodiments, the one or more arrays of wireless bipolar electrodes are placed along the bottom or floor wall(s) and the side wall(s) of the one or more fluidic microchannels.

In some embodiments, the one or more fluidic microchannels are of rectangular shape. In some other embodiments, the rectangular shaped fluidic microchannels have two side walls and one bottom or floor wall.

In some embodiments, the rectangular shaped fluidic microchannels have a width of from about 10 μm to 200 μm, or any value there between.

In some embodiments, the rectangular shaped fluidic microchannels have a depth of from about 10 μm to about 50 μm in depth, or any value there between.

In some embodiments, the one or more arrays of wireless bipolar electrodes are placed along the side walls of the rectangular fluidic microchannels. In some other embodiments, the one or more arrays of wireless bipolar electrodes are placed along the bottom wall(s) of the rectangular fluidic microchannels. In yet some other embodiments, the one or more arrays of wireless bipolar electrodes are placed along both the side and bottom walls of the rectangular fluidic microchannels.

In some embodiments, some of the bipolar electrodes have one or two ends of the bipolar electrodes placed inside a fluidic microchamber. In some embodiments, all bipolar electrodes have their two ends placed inside their corresponding microchambers. In some embodiments, none of the bipolar electrodes have their two ends placed inside their corresponding microchambers. In some other embodiments, only some of the bipolar electrodes have their two ends placed inside their corresponding microchambers.

In some embodiments, the fluidic microchamber resides inside side, bottom, top, floor, circular wall(s), or a combination thereof of the one or more fluidic microchannels. In some embodiments, the fluidic microchamber has at least one opening to the one or more fluidic microchannels.

In some embodiments, the fluidic microchamber has a width of from about 1 μm to about 200 μm, from about 2 μm to about 200 μm, from about 5 μm to about 200 μm, about 1 μm, about 2 μm, about 5 μm, about 10 μm, about 15 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, or about any value there between.

In some embodiments, the fluidic microchamber has a depth of from about 5 μm to about 50 μm, from about 10 μm to about 50 μm, from about 10 μm to about 15 μm, from about 10 μm to about 20 μm, from about 10 μm to about 25 μm, from about 10 μm to about 30 μm, from about 10 μm to about 35 μm, from about 10 μm to about 40 μm, from about 10 μm to about 45 μm, from about 15 μm to about 20 μm, from about 15 μm to about 25 μm, from about 15 μm to about 30 μm, from about 15 μm to about 35 μm, from about 15 μm to about 40 μm, from about 15 μm to about 45 μm, from about 15 μm to about 50 μm, from about 20 μm to about 25 μm, from about 20 μm to about 30 μm, from about 20 μm to about 35 μm, from about 20 μm to about 40 μm, from about 20 μm to about 45 μm, about 5 μm, about 10 μm, about 15 μm, about 20 μm, about 25 μm, about 30 μm, about 35 μm, about 40 μm, about 45 μm, about 50 μm, or about any values there between, measured from the bottom of the microchamber to the edge of the fluidic microchannel.

In some other embodiments, the microchamber has a height of from about 10 μm to about 100 μm, from about 5 μm to about 100 μm, from about 1 μm to about 50 μm, from about 10 μm to about 50 μm, from about 5 μm to about 50 μm, from about 10 μm to about 15 μm, from about 10 μm to about 20 μm, from about 10 μm to about 25 μm, from about 10 μm to about 30 μm, from about 10 μm to about 35 μm, from about 10 μm to about 40 μm, from about 10 μm to about 45 μm, from about 15 μm to about 20 μm, from about 15 μm to about 25 μm, from about 15 μm to about 30 μm, from about 15 μm to about 35 μm, from about 15 μm to about 40 μm, from about 15 μm to about 45 μm, from about 15 μm to about 50 μm, from about 20 μm to about 25 μm, from about 20 μm to about 30 μm, from about 20 μm to about 35 μm, from about 20 μm to about 40 μm, from about 20 μm to about 45 μm, about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 100 μm, or about any values there between.

In some embodiments, the distance between two adjacent microchambers is from about 5 μm to about 200 μm, from about 10 μm to about 500 μm, from about 5 μm to about 100 μm, from about 5 μm to about 50 μm, from about 5 μm to about 20 μm, from about 5 μm to about 15 μm, from about 8 μm to about 12 μm, from about 5 μm to about 30 μm, from about 10 μm to about 100 μm, from about 10 μm to about 50 μm, about 10 μm, about 5 μm, about 8 μm, about 12 μm, about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, or about any value there between. This distance is one from one edge of one microchamber to its closest edge of another microchamber.

In some embodiments, the microchambers have a dimension of 10 μm×10 μm×10 μm, 20 μm×20 μm×20 μm, 25 μm×25 μm×25 μm, 30 μm×30 μm×30 μm, 35 μm×35 μm×35 μm, 40 μm×40 μm×40 μm, 45 μm×45 μm×45 μm, 50 μm×50 μm×50 μm, or from 10 μm to 50 μm or 25 μm to 75 μm in each dimension. In some embodiments, the three dimensions of a microchamber are different from each other and vary independently.

In some embodiments, the microchambers in a microfluidic device have different dimensions or sizes, to accommodate a need to capture cells of different sizes, kinds, or other properties. A microfluidic device disclosed herein can have a distribution of various microchambers for different separations or purposes.

In some embodiments, the microchamber has a rectangular shaped cross section on the microchannel surface. In some other embodiments, the fluidic rectangular microchamber has a width of from about 1 µm to about 200 µm, or any values there between.

In some embodiments, the rectangular microfluidic chamber has a depth of from about 5 µm to about 50 µm or any value there between, measured from the bottom of the microchamber to the edge of the fluidic microchannel.

In some embodiments, the rectangular microfluidic chamber has a height of from about 10 µm to about 100 µm or any value there between.

In some embodiments, some of the bipolar electrodes have both ends in different fluidic microchannels (as in exemplary parallel-channel microfluidic devices). In this design, the spacing (from one edge of one electrode to the closest edge of the closest another parallel electrode) between two closest bipolar electrodes are is from about 5 µm to about 500 µm, from about 10 µm to about 200 µm, or any values there between.

In some other embodiments, some of the bipolar electrodes have both ends in the same fluidic microchannel (as in exemplary open-channel microfluidic devices). When the both ends of the bipolar electrodes are in the same microchannel, the spacing (from one end of one bipolar electrode to the closest one end of another bipolar electrode) between two closest bipolar electrodes in the same microchannel is from about 0.025 mm to about 0.25 mm, or any values there between.

In some embodiments, the microfluidic device has an open-channel design. As used herein, an open-channel design is referred to as an arrangement of the one or more arrays of wireless bipolar electrodes by which there are at least two arrays of wireless bipolar electrodes whose both ends are in the same microfluidic channel.

In some other embodiments, the microfluidic device has a parallel-channel design. As used herein, a parallel-channel design is referred to as an arrangement of the one or more arrays of wireless bipolar electrodes by which there are at least two arrays of wire bipolar electrodes whose both ends are in different microfluidic channels.

In some embodiments, the bipolar electrode has one or two triangular ends. In some embodiments, the bipolar electrode has both triangular ends. In some other embodiments, the bipolar electrode has a circular tip at one or two of its ends.

In some embodiments, the ends of the bipolar electrodes is from about 10 µm to about 40 µm, from about 5 µm to about 35 µm, from about 8 µm to about 12 µm, from about 5 µm to about 20 µm, from about 8 µm to about 15 µm, about 5 µm, about 8 µm, about 10 µm, about 12 µm, about 15 µm, about 20 µm, about 25 µm, about 30 µm, about 35 µm, about 40 µm, or any value there between away from the edge of the closest fluidic microchannel or the opening of the microchambers in which the bipolar electrodes reside.

In some embodiments, the distance between two adjacent wireless bipolar electrodes in the same array is from about 0.5 µm to about 500 µm, from about 1 µm to about 500 µm, from about 2 µm to about 500 µm, from about 5 µm to about 500 µm, from about 10 µm to about 500 µm, from about 10 µm to about 100 µm, from about 10 µm to about 50 µm, from about 5 µm to about 15 µm, from about 8 µm to about 12 µm, from about 20 µm to about 500 µm, from about 20 µm to about 100 µm, from about 20 µm to about 50 µm, about 0.5 µm, about 1 µm, about 2 µm, about 5 µm, about 8 µm, about 10 µm, about 12 µm, about 20 µm, about 30 µm, about 40 µm, about 45 µm, about 35 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 230 µm, about 250 µm, about 270 µm, about 290 µm, about 300 µm, about 320 µm, about 340 µm, about 360 µm, about 380 µm, about 400 µm, about 420 µm, about 440 µm, about 460 µm, about 480 µm, about 500 µm, or about any value there between. This distance is from one side edge of one bipolar electrode to its closest side edge of another electrode.

In some embodiments, the distance between two adjacent wireless bipolar electrodes in two different arrays is from about 20 µm to about 1,000 µm, from about 10 µm to about 500 µm, from about 10 µm to about 100 µm, from about 10 µm to about 50 µm, from about 5 µm to about 15 µm, from about 8 µm to about 12 µm, from about 20 µm to about 500 µm, from about 20 µm to about 100 µm, from about 20 µm to about 50 µm, about 5, about 8, about 10 µm, about 12, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 250 µm, about 300 µm, about 400 µm, about 500 µm, about 600 µm, about 700 µm, about 800 µm, about 900 µm, about 1,000 µm, or about any value there between. This distance is from one end of one bipolar electrode to the closest end of another electrode in another array.

In some embodiments, the microfluidic device further comprises a power source that is configured to have electrical communication with the ionically conductive solution and to supply an AC electric field to the ionically conductive solution.

In some embodiments, the microfluidic device is configured to generate an electric field around both ends of each bipolar electrode by capacitive charging of the electrical double layer induced at the ends of the bipolar electrode by an AC voltage only. In some other embodiments, the microfluidic device is configured to cause no faradaic reaction at both ends of the bipolar electrode by any DC voltage.

In some embodiments, the microfluidic device is configured to produce an electric field maximum in the ionically conductive solution near both ends of the bipolar electrode electrical double layer by capacitive charging of the electrical double layer induced at the ends of the bipolar electrode by an AC voltage only.

In some embodiments, the power source is configured to supply an AC with a frequency range from about 1 kHz to about 100 MHz. In some other embodiments, the power source is configured to supply an AC with a voltage range from about 1 V to about 1 kV.

In the microfluidic devices disclosed herein, the desired AC voltage and frequencies are usually supplied by a device capable for delivering such AC voltage or frequencies, such as an AC or AC/DC power supply, with or without waveform generator. In the microfluidic devices disclosed here, not every electrode are connected to the power supply. Only are the last column of electrodes (at each outer edge of the device) interconnected to a single electrical lead (driving electrode), respectively. The power supply or power source is connected to these two leads (driving electrodes).

In some embodiments, the walls of the microfluidic channels comprise a polymeric material. In some embodiments, the walls of the microfluidic channels comprise polydimethylsiloxane, polymethylmethacrylate (PMMA), glass or the like.

In some embodiments, the walls of the microchambers comprise a polymeric material. In some embodiments, the walls of the microchambers comprise polydimethylsiloxane, polymethylmethacrylate (PMMA), glass or the like.

In some embodiments, the wireless bipolar electrode comprises an electric conductor, semiconductor, or a combination thereof. In some other embodiments, the wireless bipolar electrode comprises conductive material or semi-conductive material. In yet another embodiment, the wireless bipolar electrode comprises conductive elemental metal, elemental gold, elemental platinum, elemental copper, carbon, metal oxide, indium tin oxide, or a combination thereof. In yet another embodiment, the wireless bipolar electrode comprises semi-conductive material, boron-doped diamond, or n-doped or p-doped silicon, or a combination thereof.

In some embodiments, the bipolar electrode has a width of from about 1 µm to about 50 µm, or any value there between. In some embodiments, the bipolar electrode has a thickness of from about 1 µm to about 50 µm, or any value there between. In yet some other embodiments, the bipolar electrode has a length of from about 10 µm to about 1,200 µm (1.2 mm), or any values there between. In some embodiments, the bipolar electrode has length of from about 0.1 mm to about 1.1 mm, or any values there between. In some other embodiments, the bipolar electrode has a circular cross section and a diameter of from about 5 µm to about 50 µm or any value there between.

In some embodiments, the power source comprises a waveform generator and amplifier.

In some embodiments, the one or more microchannels comprises one or more pillars close to their inlet. In some embodiments, the one or more pillars have a dimension of about 10 µm to about 200 µm, or any value there between.

In another aspect, the present invention provides a high-throughput cell isolation system. The system comprises the disclosed microfluidic device disclosed herein and an ionically conductive solution.

In some embodiments, the ionically conductive solution has a conductivity from about 1 mS/m (milli-Siemens per meter, wherein a Siemen is the inverse of an Ohms) to about 1 S/m, from about 1 mS/m to about 10 mS/m, from about 1 mS/m to about 50 mS/m, from about 1 mS/m to about 100 mS/m, from about 1 mS/m to about 200 mS/m, from about 1 mS/m to about 300 mS/m, from about 1 mS/m to about 400 mS/m, from about 1 mS/m to about 500 mS/m, from about 1 mS/m to about 600 mS/m, from about 1 mS/m to about 700 mS/m, from about 1 mS/m to about 800 mS/m, from about 1 mS/m to about 900 mS/m, from about 10 mS/m to about 50 mS/m, from about 10 mS/m to about 100 mS/m, from about 10 mS/m to about 200 mS/m, from about 10 mS/m to about 300 mS/m, from about 10 mS/m to about 400 mS/m, from about 10 mS/m to about 500 mS/m, from about 10 mS/m to about 600 mS/m, from about 10 mS/m to about 700 mS/m, from about 10 mS/m to about 800 mS/m, from about 10 mS/m to about 900 mS/m, from about 50 mS/m to about 100 mS/m, from about 50 mS/m to about 200 mS/m, from about 50 mS/m to about 300 mS/m, from about 50 mS/m to about 400 mS/m, from about 50 mS/m to about 500 mS/m, from about 50 mS/m to about 600 mS/m, from about 50 mS/m to about 700 mS/m, from about 50 mS/m to about 800 mS/m, from about 50 mS/m to about 900 mS/m, including any ranges there between.

In another aspect, the present invention provides a method isolation of a cell from a biological matrix. The method comprises contacting a biological sample with an ionically conductive solution in a fluidic device comprising one or more wireless bipolar electrodes and applying an AC electric field to the ionically conductive solution for a period of time so a targeted cell is trapped at the tip of the bipolar electrode or aggregated at a point where the electric field is a local maximum; wherein the biological sample contains a targeted cell to be isolated.

As used herein, a biological sample is any sample taken from a live system or derived from a sample taken from a live system. The biological sample as used here is referred to as any collection of samples containing multiple live cells. The biological sample as used herein includes blood or plasma samples taken from an animal or samples that are processed by other procedures, but originated from blood or plasma.

As used herein, a target cell is one that can undergo dielectrophoresis.

In some embodiments, the one or more wireless electrodes are in one or more microchambers, respectively.

In yet another aspect, the present invention provides a method of isolating a cell, especially a rare cell, from a biological matrix. The method comprises contacting a biological sample with an ionically conductive solution in any of the microfluidic devices disclosed herein and applying an AC electric field to the ionically conductive solution and the wireless bipolar electrodes for a period of time so a targeted cell is trapped at the tip of the bipolar electrode or aggregated at a point where the electric field is a local maximum; wherein the biological sample contains the targeted cell to be isolated.

In some embodiments, the ionically conductive solution has a linear flow velocity or flow rate of from about 0 µm/s to about 120 µm/s, about 0.1 µm/s to about 120 µm/s, about 0.1 µm/s to about 80 µm/s, from about 5 µm/s to about 110 µm/s, from about 10 µm/s to about 100 µm/s, from about 15 µm/s to about 105 µm/s, from about 20 µm/s to about 100 µm/s, from about 25 µm/s to about 95 µm/s, from about 30 µm/s to about 90 µm/s, from about 25 µm/s to about 95 µm/s, about 20 µm/s, about 30 µm/s, about 35 µm/s, about 40 µm/s, about 45 µm/s, about 50 µm/s, about 55 µm/s, about 60 µm/s, about 65 µm/s, about 70 µm/s, or any value there between.

In some embodiments, the method uses an array of bipolar electrode comprising only one bipolar electrode. In some embodiments, the method does not use any DC electric field.

In some other embodiments, the method further comprises washing the one or more fluidic microchannels with an ionically conductive solution. In some other embodiments, the method further comprises collecting the targeted cell.

In some embodiments, the method is used to the targeted cell that is a circulating tumor cell (CTC). In some other embodiments, the biological matrix is a mixture of different cells. In yet some other embodiments, the biological matrix is a blood sample.

In some embodiments, the AC electric field applied in the fluidic device is a series of AC electric fields with different frequencies and voltages. In some embodiments, the targeted cell undergoes a positive DEP response. In some other embodiments, the targeted cell undergoes a negative DEP response.

In some other embodiments, the method has throughput of from about 0.01 mL/h to about 30 mL/h, from about 0.01 mL/h to about 0.5 mL/h, from about 0.01 mL/h to about 1 mL/h, from about 0.01 mL/h to about 2 mL/h, from about 0.01 mL/h to about 4 mL/h, from about 0.01 mL/h to about 6 mL/h, from about 0.01 mL/h to about 8 mL/h, from about 0.01 mL/h to about 10 mL/h, from about 0.01 mL/h to about 12 mL/h, from about 0.01 mL/h to about 14 mL/h, from about 0.01 mL/h to about 16 mL/h, from about 0.01 mL/h to about 18 mL/h, from about 0.01 mL/h to about 20 mL/h, from about 0.01 mL/h to about 22 mL/h, from about 0.01 mL/h to about 24 mL/h, from about 0.01 mL/h to about 26 mL/h, from about 0.01 mL/h to about 28 mL/h, from about 0.1 mL/h to about 0.5 mL/h, from about 0.1 mL/h to about 1 mL/h, from about 0.1 mL/h to about 2 mL/h, from about 0.1 mL/h to about 4 mL/h, from about 0.1 mL/h to about 6 mL/h, from about 0.1 mL/h to about 8 mL/h, from about 0.1 mL/h to about 10 mL/h, from about 0.1 mL/h to about 12 mL/h, from about 0.1 mL/h to about 14 mL/h, from about 0.1 mL/h to about 16 mL/h, from about 0.1 mL/h to about 18 mL/h, from about 0.1 mL/h to about 20 mL/h, from about 0.1 mL/h to about 22 mL/h, from about 0.1 mL/h to about 24 mL/h, from about 0.1 mL/h to about 26 mL/h, from about 0.1 mL/h to about 28 mL/h, from about 0.1 mL/h to about 30 mL/h, from about 0.5 mL/h to about 0.5 mL/h, from about 0.5 mL/h to about 1 mL/h, from about 0.5 mL/h to about 2 mL/h, from about 0.5 mL/h to about 4 mL/h, from about 0.5 mL/h to about 6 mL/h, from about 0.5 mL/h to about 8 mL/h, from about 0.5 mL/h to about 10 mL/h, from about 0.5 mL/h to about 12 mL/h, from about 0.5 mL/h to about 14 mL/h, from about 0.5 mL/h to about 16 mL/h, from about 0.5 mL/h to about 18 mL/h, from about 0.5 mL/h to about 20 mL/h, from about 0.5 mL/h to about 22 mL/h, from about 0.5 mL/h to about 24 mL/h, from about 0.5 mL/h to about 26 mL/h, from about 0.5 mL/h to about 28 mL/h, or from about 0.5 mL/h to about 30 mL/h, including any ranges there between, of the biological matrix.

In some other embodiments, the method has throughput of from about 1 mL/h to about 30 mL/h, from about 1 mL/h to about 2 mL/h, from about 1 mL/h to about 5 mL/h, from about 1 mL/h to about 10 mL/h, from about 1 mL/h to about 15 mL/h, from about 1 mL/h to about 20 mL/h, from about 1 mL/h to about 25 mL/h, from about 1 mL/h to about 50 mL/h, including any ranges there between, of the biological matrix.

In some other embodiments, the method has throughput about 0.01 mL/h, about 0.02 mL/h, about 0.05 mL/h, about 0.08 mL/h, about 0.1 mL/h, about 0.2 mL/h, about 0.4 mL/h, about 0.6 mL/h, about 0.8 mL/h, about 1 mL/h, about 2 mL/h, about 3 mL/h, about 4 mL/h, about 5 mL/h, about 6 mL/h, about 8 mL/h, about 10 mL/h, about 12 mL/h, about 14 mL/h, about 16 mL/h, about 18 mL/h, about 20 mL/h, about 22 mL/h, about 24 mL/h, about 26 mL/h, about 28 mL/h, or about 30 mL/h, including any ranges there between, of the biological matrix.

Significantly, the disclosed microfluidic devices communicate an AC field across insulating barriers (microchannel walls) thus enabling the simultaneous capture cells, such as CTCs, across parallel microchannels. Microchambers aligned to the BPE tips and embedded along the wall of each microchannel provide discreet capture sites with defined volume, thus enabling single-cell capture or with an additional selection based on size of the microchambers or other attributes (length, spacing, shape, distribution of BPEs and microchannels, and etc.) for the BPEs, microchannels, microchambers, power source, or a combination thereof. Moreover, the use of wireless electrodes removes the need to provide ohmic contact to each electrode, thus simplifying the device design and fabrication process. This feature provides unparalleled flexibility for DEP schemes that access large sample volumes along all axes. Finally, the disclosed invention can isolate and fully release captured cells and to retain cell viability at the same time, a requirement for the downstream analysis of cells, such as culturing and testing of drug efficacy. The disclosed devices prove to be useful in further studies centering upon the selective capture of CTCs from blood for the establishment of diagnosis and prognosis of cancer and for the evaluation of anticancer therapies.

The disclosure also provides an inexpensive and practical platform for parallel DEP cell manipulation with extended, tunable regions of strong DEP force. This technology employs BPEs to modulate the local conductivity of an aqueous medium through the generation of ion depletion and enrichment zones. Cells would be trapped at the resulting electric field maxima or minima. Importantly, this technology addresses each of the shortcomings of existing DEP technology. First, BPEs can be operated in an array format without requiring wire leads (electrical contact) to each individual BPE. As a result, the device is simple to fabricate and requires low operating voltages. Second, the electric field gradients, which exert DEP force on the cells, have controllable size and can traverse the microchannel cross-section. This feature is important because the device dimensions and throughput are not limited by short-range DEP forces. Finally, the trapping zones in the disclosed invention can be mobilized through the introduction of sufficient fluid flow. This characteristic is advantageous because it allows cells to be transported for downstream analysis while remaining trapped.

Furthermore, the wireless BPEs with the triangular ends and round tips as used in some of the disclosed microfluidic devices also made it possible to capture a single cell or microemboli of cells and to have more wireless electrodes in the same footprint.

The current disclosure has demonstrated that the integration of wireless electrodes allows for the creation of DEP microfluidic devices that are easily scalable along the x- and y-directions, which increases throughput.

Furthermore, due to the incorporation of microchambers into the parallel-channel design of the disclosed microfluidic devices, single-cell capture was readily achieved by adjusting the size of microchambers to the size of the targeted cells. In fact, the sizes of the microchambers, shapes or tips of the BPEs, and/or other parameters in a microfluidic device disclosed herein do not have to be uniform and can be different to capture a cell or microemboli of cells. For examples, a microfluidic device can be configured to capture single cells upstream, but capture microemboli of the same cells downstream, by using the different sizes for the microchambers. Other attributes of the microchannels, microchambers, BPEs, voltage and frequency of the AC field, or a combination thereof can also be adjusted to avoid capturing a single cell, to capture single cells or microemboli of cells, or anything in between, for various purposes.

Similarly the length and spacing between them do not have to be uniform in an open-channel microfluidic device disclosed herein. In fact, the length and spacing of the BPEs are important factors for capturing cells or microemboli of cells.

The disclosed microfluidic devices exhibit significant advancements in DEP technology including wireless control of the AC field and enhanced design flexibility, which led to increased throughput and high-fidelity parallel single-cell capture. These advancements are made while retaining the inherent advantages of DEP including selective and label-free isolation of cells and ease of fabrication, which provide an avenue to utilize the disclosed microfluidic devices for point-of-care applications, not only as a result of its ability to isolate single CTC cells, but also as a result of its flexibility to capture other type of cells or mixture of multiple cells. The captured cells can be isolated, accumulated, and then used for its characterizations, such as its invasiveness and response to various drugs. The microfluidic devices disclosed herein have potential clinic applications, such as for accurate disease diagnosis and selection of effective treatment.

All publications, patent applications, issued patents, and other documents referred to in this specification are indicative of the level of ordinary skill in the art to which this invention pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

The present invention is further illustrated by the following examples, which should not be considered as limiting in any way.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Chemicals and Cell Culture

Chemicals

The silicone elastomer, curing agent (Sylgard 184), bovine serum albumin (BSA) (biotech grade) and 0.25% Trypsin-EDTA (1×) were purchased from Fisher Scientific (Thermo Fisher Scientific, Inc., Waltham, Mass.). The DMEM/F12 media, dextrose (d-glucose), sucrose, Pluronic® F-108 and 1.0 M Tris-HCl stock were obtained from Sigma-Aldrich, Inc. (St. Louis, Mo.). The RPMI 1640 media was purchased from American Type Culture Collection (ATCC) (Manassas, Va.). All dilutions were conducted with Milli-Q water (18.0 MΩ·cm). DEP buffer was comprised of 8.0% sucrose, 0.3% dextrose, and 0.1% BSA in 1.0 mM Tris buffer (pH 8.1).

Cell Culture

MDA-MB-231 and Jurkat E6-1 T cells were obtained from ATCC. They were cultured in DMEM/F12 and RPMI 1640 media, respectively with 1% pen-strep and 10% fetal bovine serum supplemented at 37° C. and 5% $CO_2$. All cells were subcultured every 2-3 days to maintain the concentration of cells less than $1\times10^6$ cells/mL. In preparation of DEP experiments, MDA-MB-231 cells were detached from culture flask using 0.25% Trypsin-EDTA (1×), followed by pelleting by centrifugation (1.1 rpm, 5 min) and resuspension in 5 mL Tris DEP buffer. Jurkat E6-1 T cells were directly pelleted from culture medium prior to resuspension in DEP buffer. Pelleting and resuspension was repeated to wash cells twice in DEP buffer before DEP capture experiments.

Example 1

Fabrication of Some Exemplary Devices

Some exemplary high-throughput microfluidic devices were fabricated using standard photolithography and etching processes. First, BPE arrays were patterned using positive photoresist (AZ 400K; Microchem Co., Ulm, Germany) on glass slides coated with a layer of 50 Å chromium (Cr) elemental and another layer of 1000 Å elemental gold (Au), followed by wet-etching the gold layer by gold etchant ($KI:I_2:H_2O=4$ g:1 g:40 mL) and then the chromium layer by chromium etchant (Sigma Aldrich, St. Louis, Mo.), respectively. Acetone was applied to dissolve the remaining photoresist. Second, channels were molded using a positive photoresist (SU-8 2025; Microchem Co., Westborough, Md.) patterned on a silicon substrate. Subsequently, polydimethylsiloxane (PDMS) precursor was poured on the SU-8 mold and cured at 70° C. for 2 h.

The alignment of PDMS microchannels with the BPE arrays was carried out as follows. First, the patterned gold slides and PDMS microchannels were exposed to oxygen plasma (Plasma cleaner, Harrick Scientific, Ithaca, N.Y.) for 90 second to activate the surfaces for permanent bonding. Second, a few drops of ethanol were applied on both surfaces to delay bonding and facilitate the alignment. Third, the aligned device was baked at 70° C. for 2 h to completely drive off the ethanol and to encourage bonding. Finally, 3 NM Pluronic in 1.0 mM DEP buffer was injected into the microchannels via vacuum (to remove entrapped air) and kept at room temperature overnight to coat the microchannel surface, thus reducing non-specific adsorption of cells to the channel surface and eliminating electroosmotic flow (EOF). After coating with Pluronic, all channels were rinsed with DEP buffer for 15 min before DEP experiments.

Figure 3A:
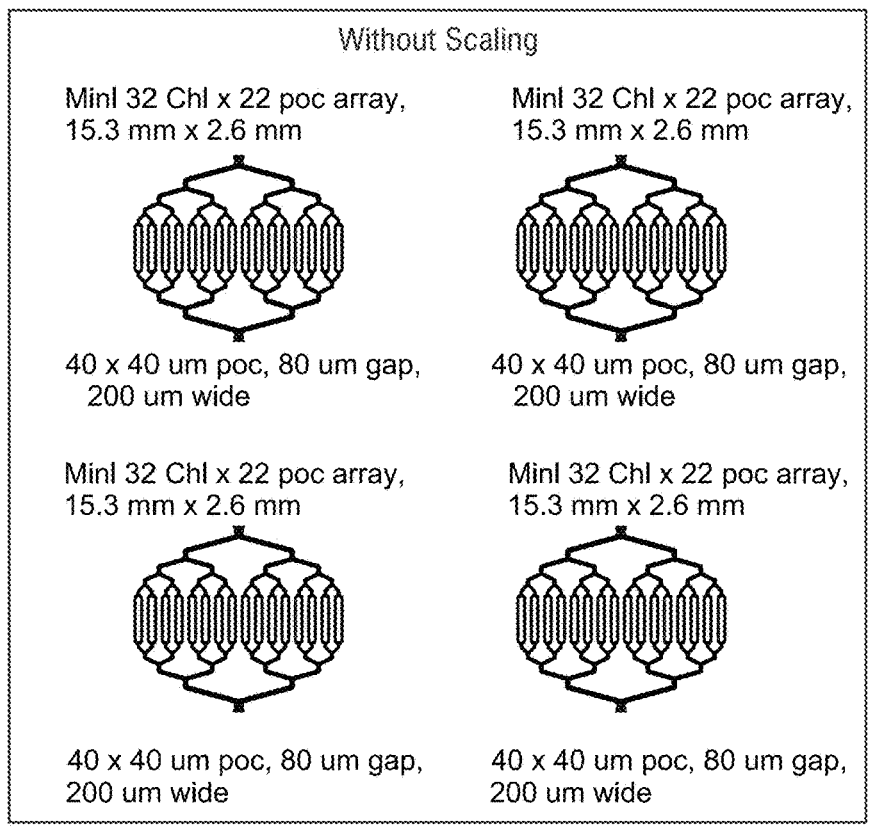
FIG. 3A shows an exemplary arrangement of the microchannels of a parallel-channel design.

For an exemplary claimed device in parallel-channel design, 32 microchannels with each being 2.95 mm long× 200 μm wide×25 μm tall were arranged in parallel and separated by 0.286 mm. Each microchannel had 22 microchambers extruded at each side. Each microchamber was 40 μm×40 μm and the distance of two adjacent microchambers was 80 μm. Two microchannels were then merged to one merged microchannel and further connected with another merged microchannel and so forth to form a tree-like device. FIG. 3A shows an exemplary arrangement of the microchannels of a parallel-channel design. Diamond-shaped pillars (100 μm×40 μm) were introduced at the microchannel inlets to facilitate cells flowing into the microchannels. The electrodes extend into the microchambers with a 10 μm distance away from the microchannel. The two rows of electrodes at the end were connected and lead to contact for the waveform generator.

Figure 3B:
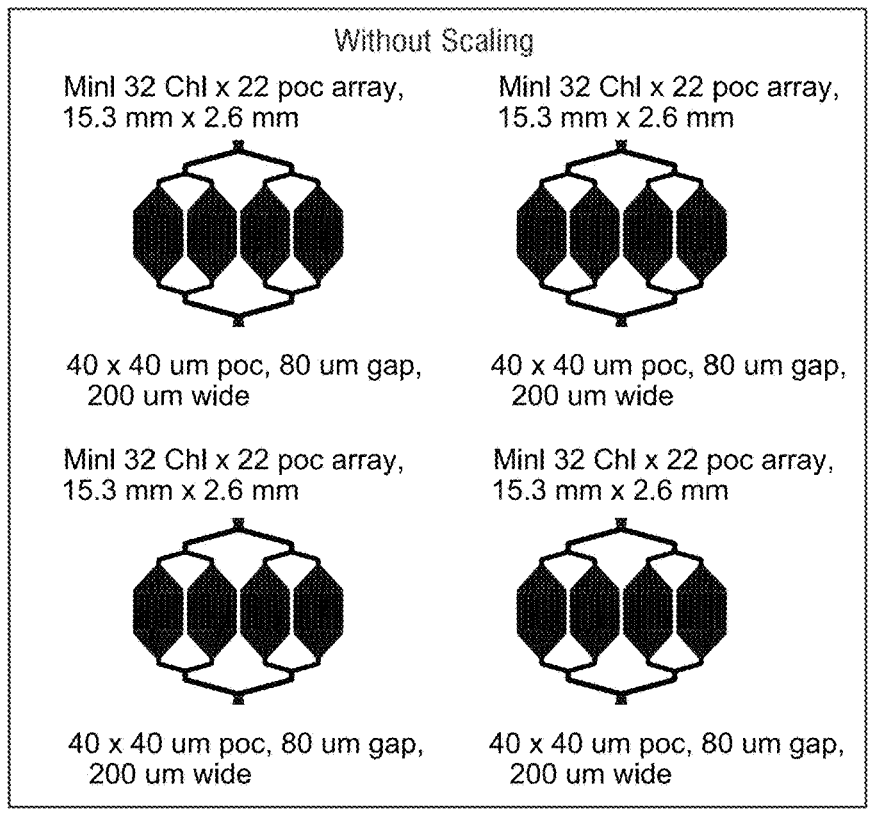
FIG. 3B shows an exemplary arrangement of the microchannels of an open-channel design.

An exemplary claimed device in open-channel design was made in a similar procedure, except with the following modifications. First, 8 microchannels were merged into one by deleting all the channel walls. This resulted in 4 main microchannels interconnected with BPEs. Second, pillars with a radius of 20 μm were added between the tips of the electrodes to support the ceiling. Finally, all the branches were edited in a way that each reservoir branched into two microchannels in which each individual microchannel was merged from the two main microchannels. FIG. 3B shows an exemplary arrangement of the microchannels of an open-channel design. Consequently, the separation area of the open-channel design doubled compared to the parallel-channel design at the same footprint.

Example 2

Trap Jurkat Cells with Only One BPE or BPE Array with AC Only

Figure 4A:
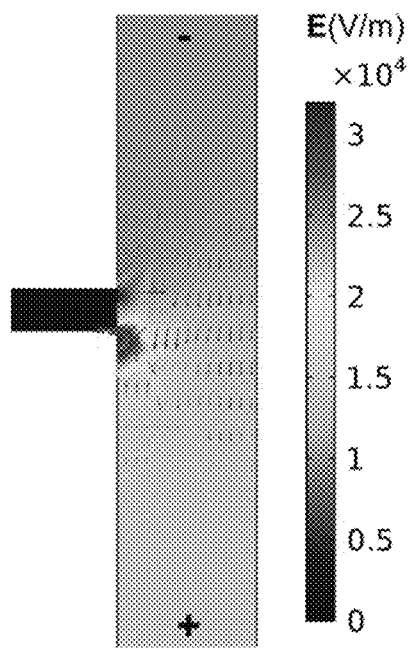
FIG. 4A shows a simulated electric field map with one BPE in a chamber.
Figure 4B:
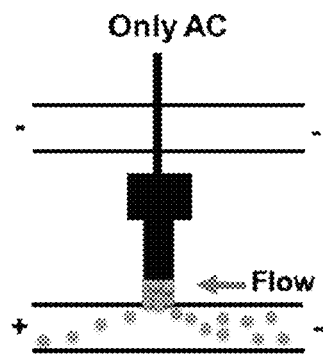
FIG. 4B shows a scheme of the setup with one BPE and an application of only an AC field.
Figure 4C:
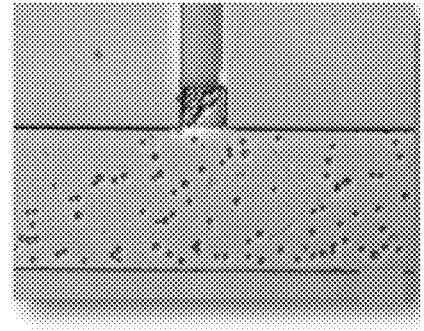
FIG. 4C shows an optical micrograph of Jurkat cells in an experiment using Jurkat E6-1 T-cells in DEP buffer (8.0% sucrose, 0.3% dextrose, 0.1% bovine serum albumin, and 1 mM Tris.HCl (pH 8.0)), 64 Vpp (volts peak-to-peak) AC at 80 kHz, and a fluid flow velocity of 30 μm/s. The microchannels used here were 200 μm wide×25 μm tall×4 mm long.
Figure 4D:
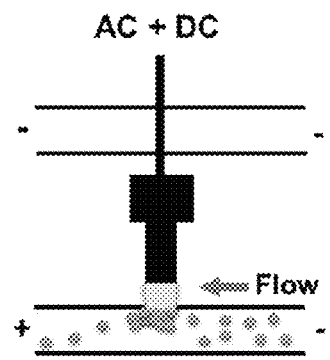
FIG. 4D shows a scheme of the setup with one BPE and an application of AC and DC field.
Figure 4E:
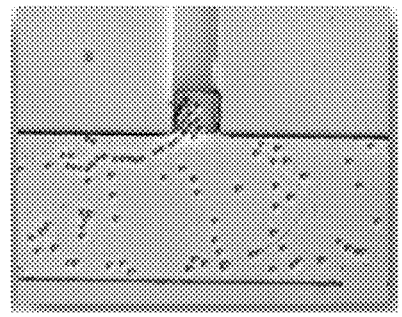
FIG. 4E shows an optical micrograph of Jurkat cells in the same experimental design as FIG. 4C with the addition of 3.2 V DC bias.

When AC was applied, the higher field intensity of the chamber of the electric field was at the side of the positive driving electrode. FIG. 4A shows a simulated electric field map with one BPE in a chamber. When a frequency with nDEP for Jurkat cells applied, Jurkat cells were tapped into the chamber when buffer solution flew from the side of negative driving electrode as illustrated in FIG. 4B. FIG. 4C shows an optical micrograph of Jurkat cells in an experiment using Jurkat E6-1 T cells in DEP buffer (8.0% sucrose, 0.3% dextrose, 0.1% bovine serum albumin, and 1 mM Tris.HCl (pH 8.0)), 64 Vpp (volts peak-to-peak) AC at 80 kHz, and a fluid flow rate or linear flow velocity of 30 μm/s. The microchannels used here were 200 μm wide×25 μm tall×4 mm long. However, when 3.2 V DC was added, water could be reduced to $OH^-$ and neutralized by $TrisH^+$ in the buffer solution to form an ion depletion zone (IDZ). Due to the exclusion of charged species in the IDZ, cells trapped were expelled from the chamber as illustrated in FIG. 4D. FIG. 4E shows an optical micrograph of Jurkat cells in the same experimental design as FIG. 4C with the addition of 3.2 V DC bias.

In addition, DC was also not desired considering the following consequences. First, the opposite polarity of two parallel microchambers at the two sides of a microchannel causes the formation of IDZ at one side and ion enrichment zone (IEZ) at the other side. The IDZ leads to the repulsion of cells while the IEZ causes the attraction of cells. Contact with the IDZ may cause lysis of cells because of the exponentially increased high electric field in that IDZ (due to low ionic strength and high electrical resistance). Second, electrophoretic force is introduced and competes with DEP force when DC is introduced. Third, joule heating may become significant under DC electric field. Herein, only AC electric field was utilized in the experiments with the claimed microfluidic device with a BPE array.

Example 3

BPE Electrode Optimization

To optimize BPE and channel design, COMSOL simulation software (COMSOL Multiphysics 5.2a, Los Angeles, Calif.) was employed. The dimensions used in the simulations are as follows. The channels were 100 μm wide with 60 μm (long)×60 μm (wide) pockets separated by 120 μm (edge-to-edge distance). The tip of each of the BPEs is overlapped with the outer edge of a microchamber. The voltage difference applied between adjacent BPEs is 4 Vpp, leading to the averaged electric field of 40 kV/m.

In this example, two exemplary shapes, triangle and square for a BPE electrode used in a BPE array is investigated through simulation. For the simulation, COMSOL Multiphysics (COMSOL, Inc., Los Angeles, Calif.) software Electrostatics Module was used to create a 2D plot of the electric field distribution that results upon application of a potential bias across a representative device. The material properties (dielectric constants) for polydimethylsiloxane, the metallic BPEs, and water were specified. FIG. 5A shows the electric field simulation in an array-based design using square BPE and FIG. 5B shows the electric field simulation in an array-based design using triangle BPE. As the simulation shows, the highest electric field locates at the corner of each square BPE, while the electric field reaches maximum at the electrode tips for a triangular BPE. Therefore, BPEs with triangular tips are beneficial for positioning cells at the center of each microchamber.

In addition, since the highest electric field using triangle BPEs is centralized at the tip and this overly focused field may result in a loss of cell viability, the BPEs used in the following Examples were further rounded with a radius of 5 μm. These rounded tips distribute an electric field with the strongest region over a broader area, thereby reducing the possible damage to cells.

An additional advantage of using a BPE with triangular shape, because of its capability for a highly focused electric field, is that the microchannel width could be doubled to increase the throughput while maintaining the good performance of trapping cells.

Example 4

BPE Array Arrangement Optimization

Figures 6A, 6B:
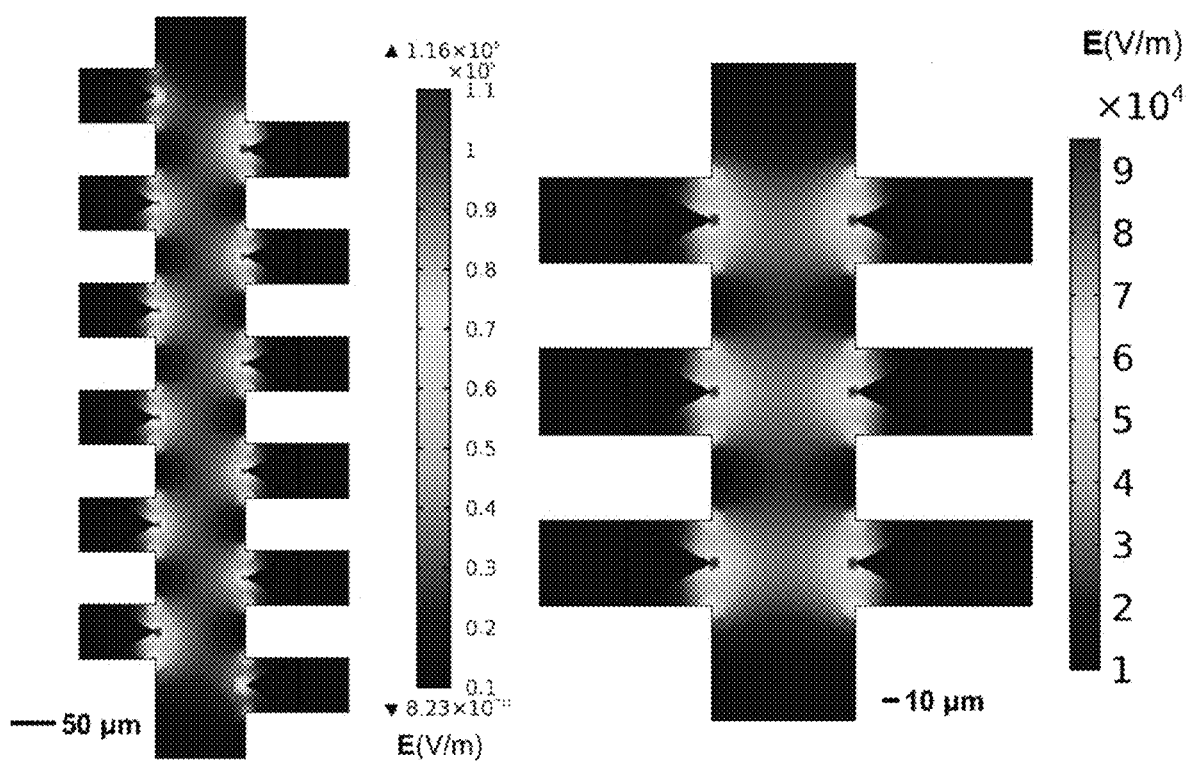
FIG. 6A shows a simulated electric field in a BPE array device using a large number of staggering triangular BPEs.
FIG. 6B shows a simulated electric field in a BPE array device using a large number of parallel triangular BPEs.

Similar simulation shows a parallel arrangement for BPE arrays yield a more uniform electric field with the strongest field strength at each triangular BPE tip. FIG. 6A and FIG. 6B show the simulated electric field in a staggering and parallel arrangement, respectively. As shown in FIG. 6A, a single BPE has a non-uniform electric field. This non-uniform electric field would cause more cells trapped at one side than the other and therefore not ideal for capturing a single-cell. Though this non-uniformity will be significantly diminished when increasing the number of BPEs in a staggering arrangement as shown in FIG. 5A and FIG. 5B, it may still cause some non-uniformity at some locations. A parallel arrangement of triangular BPE array yields a more uniform electric field as shown in FIG. 6B around each triangular tip and therefore is preferred to capture cells around the tip. Herein, parallel BPEs were chosen in the following experiments.

Example 5

BPE Tip Position Optimization

Figure 7A:
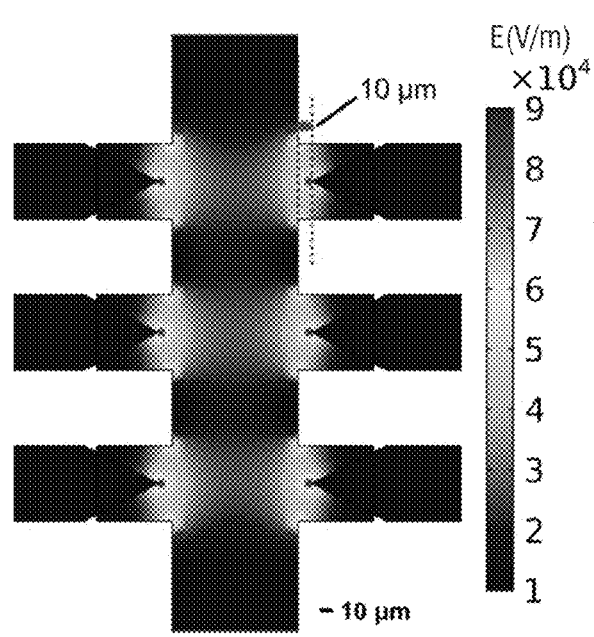
FIG. 7A shows a simulated electric field simulation with the BPE tip being 10 μm away from the edge of the channel.
Figure 7B:
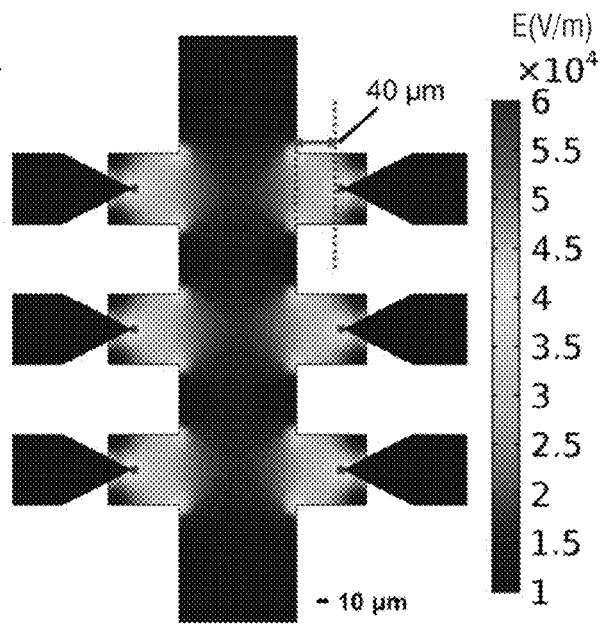
FIG. 7B shows a simulated electric field simulation with the BPE tip being 40 μm away from the edge of the channel.

Since it is possible that a fast fluid flow may wash away the cells trapped at the tip of BPE electrodes in the parallel-channel design, the positions of BPE tips relative to the microchannels were investigated for better cell capture efficiency. An electric field simulation with two different tip positions are shown in FIG. 7A and FIG. 7B, respectively. As shown in FIG. 7B, the electric field along the microchannel becomes too weak to trap cells if a BPE tip is 40 μm away from the channel. However, if the distance is 10 μm as shown in FIG. 7A, which is comparable to the radius of a MDA-MB-231 cell, a cell is expected to be trapped inside a microchamber and avoid being carried away by drag force. Based on the above considerations, a design with 10 μm distance between a channel and BPE tip was selected for the following Examples.

Example 6

DEP Characterization of Two Model Cell Lines

Figure 8A:
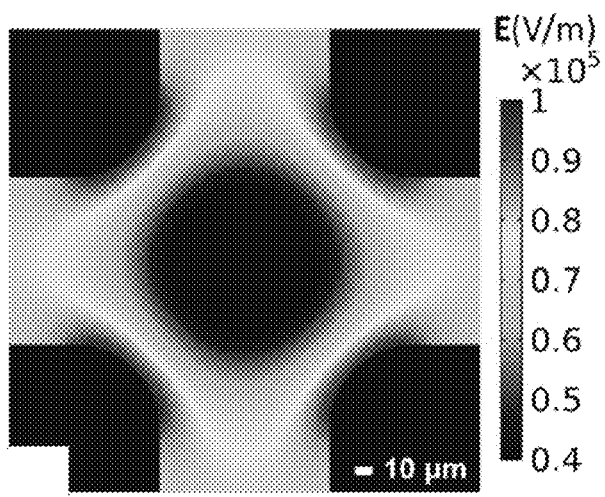
FIG. 8A shows a simulated electric field with a quadrupole electrode design.

To test the ability of our BPE array-based microfluidic device to separate CTCs from blood, two model cell lines were employed. The DEP responses of MDA-MB-231 (breast cancer cells) and Jurkat T-cells (white blood cells) were characterized using quadrupole electrodes as follows to determine an AC electric field frequency at which the two cell types could be separated. The conductivity of the Tris DEP buffer used in the present work was 6.2 mS/m. The quadrupole electrode design was guided by simulation of the resulting electric field using COMSOL simulation software as shown in FIG. 8A. In this simulated electric field, the strongest field was around each electrode and the minimum field was at the center of the quadrupole. The design was found to provide a sufficient electric field gradient to allow nDEP and pDEP responses of the cells to be distinguished. Cells undergoing nDEP moved to the center of the quadrupole design at which the electric field was at a minimum. In contrast, a pDEP response was characterized by cells moving to the electrode edges, where the electric field was strongest.

Figure 8B:
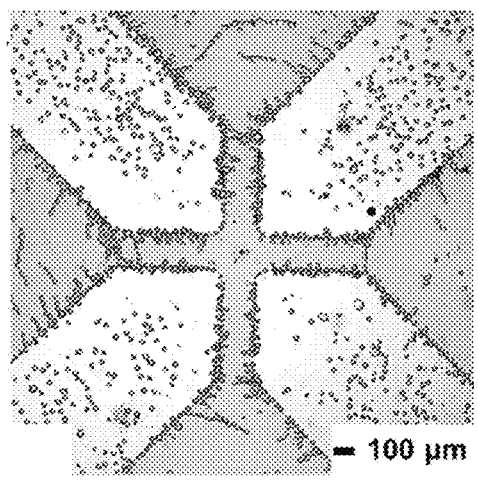
FIG. 8B shows the positions of MDA-MB-231 cells undergoing pDEP at 40 kHz in DEP buffer (8.0% sucrose, 0.3% dextrose, 0.1% bovine serum albumin, and 1.0 mM Tris.HCl (pH 8.0)).
Figure 8C:
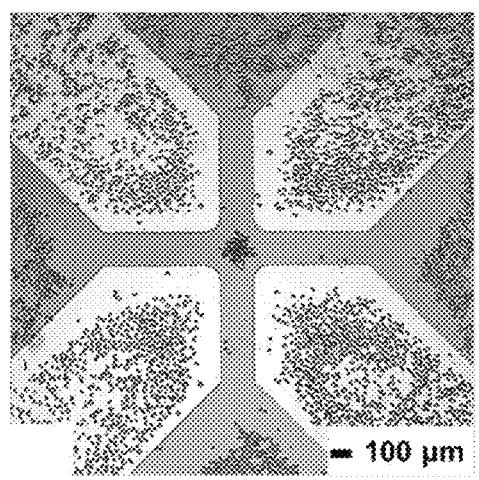
FIG. 8C shows the positions of Jurkat E6-1 T-cells undergoing nDEP at 40 kHz in DEP buffer (8.0% sucrose, 0.3% dextrose, 0.1% bovine serum albumin, and 1.0 mM Tris.HCl (pH 8.0)).

To determine the response of each model cell line, a 100 µL, droplet cell sample (1×106 cells/mL in Tris DEP buffer) was applied to the quadrupole electrodes and the frequency of the AC voltage applied between opposing electrode pairs was swept from 1 kHz to 100 kHz. The quadruple electrodes were designed with 500 µm width and 100 µm gap between adjacent edges. The electrodes were connected to a Tektronix AFG3011C waveform generator (Tektronix, Beaverton, Oreg.) with copper tape. After adding 100 µL, of the cell suspension to the quadrupole electrodes, a glass coverslip was placed on top. 10 Vpp was applied between neighboring electrodes, and images were taken after 3 min to determine whether cells underwent a pDEP or nDEP response. Subsequently, the frequency was increased in 10 kHz increments over the range of 1 kHz to 100 kHz. Results indicated that MDA-MB-231 cells experienced strong pDEP from 40 kHz to 70 kHz, while the majority of Jurkat-E6 T cells underwent an nDEP response (a few Jurkat cells were attracted on the edges of the electrodes from 50 kHz to 70 kHz). Therefore, a 40 kHz AC field was chosen for separation as MDA cells experienced strong pDEP and Jurkat cells underwent an nDEP response. FIG. 8B shows the positions of MDA-MB-231 cells undergoing pDEP at 40 kHz in DEP buffer (8.0% sucrose, 0.3% dextrose, 0.1% bovine serum albumin, and 1 mM Tris.HCl (pH 8.0)) and FIG. 8C shows the positions of Jurkat E6-T cells undergoing nDEP in the same DEP buffer.

Example 7

Electric Field Simulation of Two Exemplary BPE Array Devices

Figure 9A:
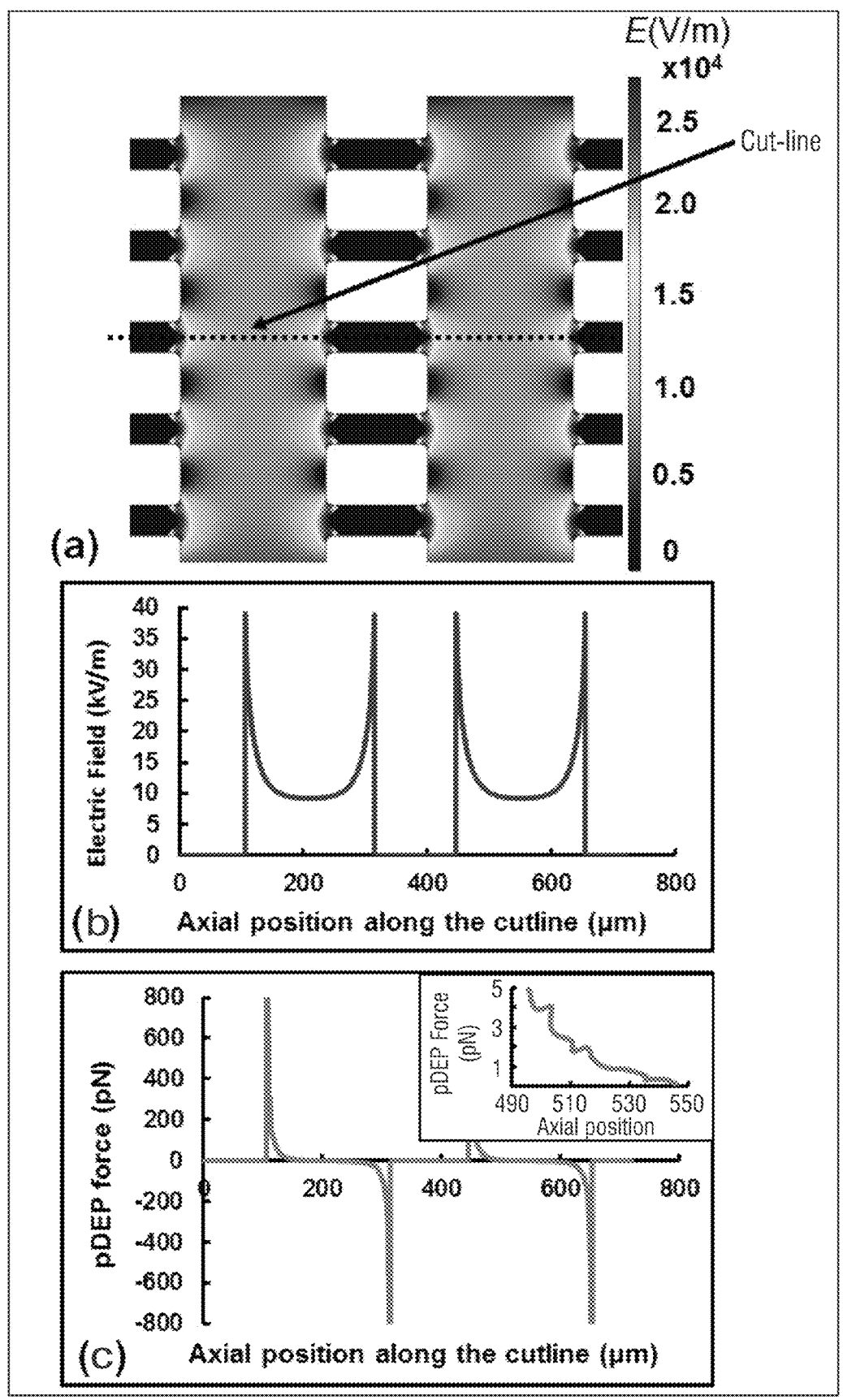
FIG. 9A shows a simulated electric field strength and DEP force in a parallel-channel design.
Figure 9B:
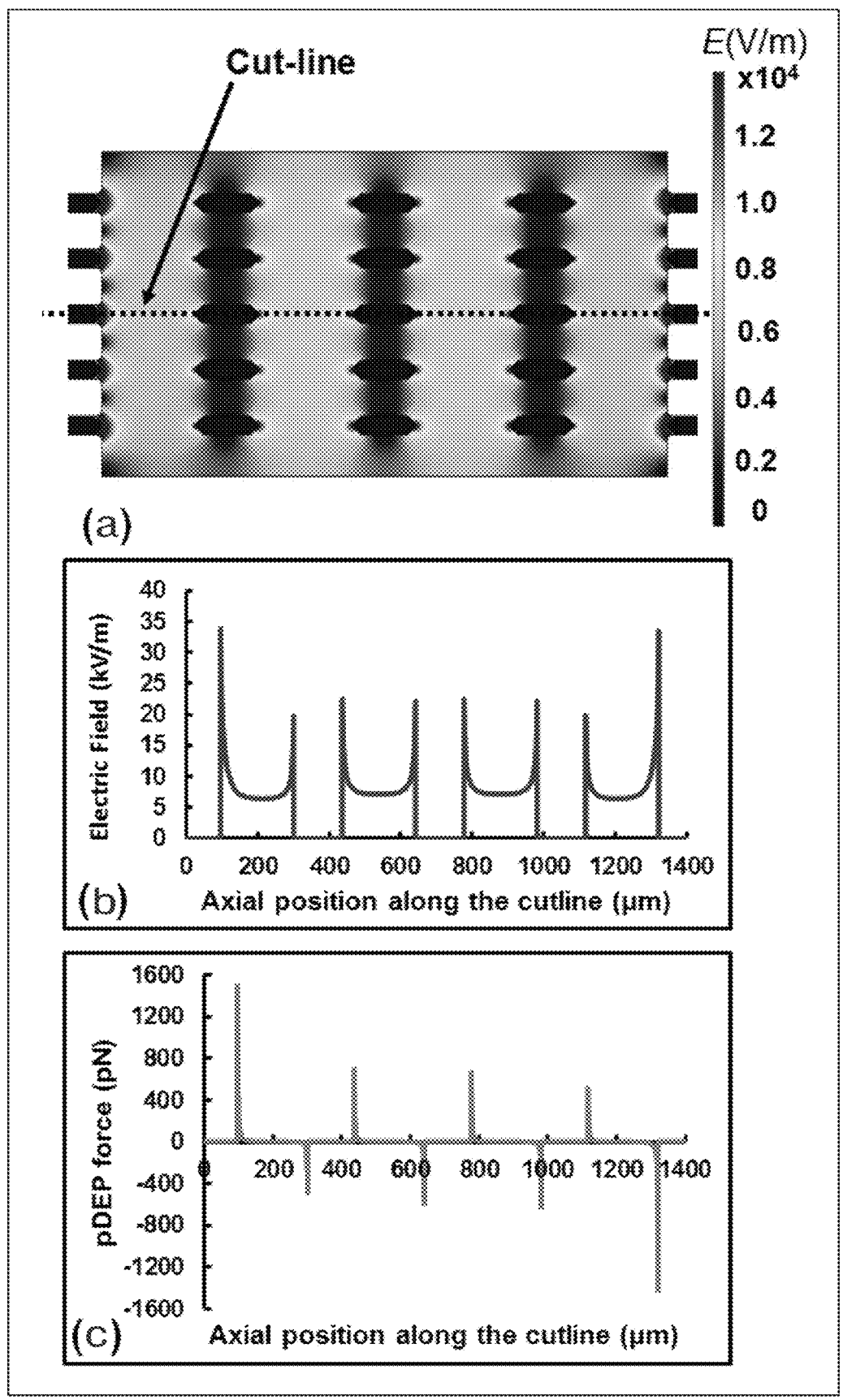
FIG. 9B shows a simulated electric field strength and DEP force in an open-channel design. Inset of (c) shows the detail of the DEP force at distances greater than 54 μm from the BPE tip.

Two designs were fabricated and investigated using BPEs to shape the AC electric field. The parallel-channel design had 32 parallel microchannels interconnected with BPEs while the open-channel design featured four large (2.58 long×3.68 mm wide) open microchannels containing BPE arrays and further linked by BPEs. The distribution of the electric field in these two devices was simulated using the finite element method (COMSOL Multiphysics 5.2a). FIG. 9A shows a simulated electric field strength and DEP force in a parallel-channel design. FIG. 9B show a simulated electric field strength and DEP force in an open-channel design. Inset of (c) in FIG. 9B shows the detail of the DEP force at distances greater than 54 µm from the BPE tip. In FIG. 9A and FIG. 9B, the distribution of the electric field and the DEP force along a line trace intersecting the central axis of the BPEs in the two optimized devices are shown.

In this simulation, the dimensions (e.g., channel width, pocket size and BPE tip position and shape) matched those of devices employed in the other experiments. The spatially and time-averaged electric field ($E_{avg,rms}$) was 13.7 kV/m, and 6.0 kV/m for the parallel-channel and open-channel design, respectively. These values correspond to an applied voltage of 248 Vpp, which was employed in experiments. In FIG. 9A and FIG. 9B, panels (a) show the resulting electric field distribution in each design, respectively, and panels (b) are plots of the electric field strength along cut-lines bisecting a row of BPEs. The maximum electric field strength is located at the BPE tips and is approximately 38 kV/m, and 34 kV/m for the parallel-channel and open-channel design, respectively. In FIGS. 9A and 9B, panels (c) show an estimate of the pDEP force experienced by a 12.0 µm-radius cell as a result of this electric field (Re[K(ω)]=1.0).

As shown in FIG. 9A and FIG. 9B, the electric field showed the maximum value around the BPE tips for both device designs. In both designs, cells experiencing pDEP were expected to be trapped at the electric field maxima around the BPE tips, while cells undergoing nDEP remain in fluid flow.

As shown in FIG. 9A and FIG. 9B, the DEP force exerted by the electric field is sufficient for cell trapping. A force of 5.0 to 15 pN is sufficient to overcome drag force experienced by an MDA cell trapped in fluid flowing past at linear velocities in the range employed in the experiments reported here. Importantly, pDEP forces greater than this threshold extend up to 50 µm from each BPE tip (inset of FIG. 9B, panel (c), BPE tip located at 446 µm). This result is significant because it indicates that channels wider than 100 µm will experience a decrease in capture efficiency as channel width increases.

In the parallel-channel device, all the tips were positioned inside microchambers with a 10 µm gap between the tip and the microchamber opening which prevented captured cells from being pulled away by the flowing DEP buffer. Using this approach, a relatively high flow rate or liner flow velocity could be implemented in parallel-channel design. In contrast, the total separation channel width increased when changing to the open-channel design which also results in high-throughput. Also demonstrated by the results in FIG. 9A and FIG. 9B was the impact of rounding the BPE tips on the electric field distribution. In comparison to the fully pointed tips shown in FIG. 2E, these rounded tips distribute the strongest region of the electric field over a broader area, thereby preventing the damage to cells that may be incurred by an overly focused electric field.

FIG. 9B also shows that the electric field distribution in the open-channel design, the field strength around the junctions between the large open chambers (34 kV/m) is 35% higher than that toward the middle of the chambers (22 kV/m). Thus, more cells were expected to be trapped around the junctions. In contrast, the electric field profile is uniformly distributed across the parallel channels, therefore a uniform distribution of trapped cells can be expected.

Example 8

Evaluation of BPE Array Device in Parallel-Channel Design for Cell Separation

Figure 10A:
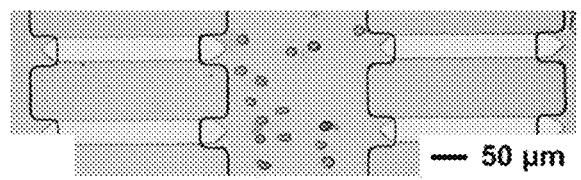
FIG. 10A shows the bright field image of the MDA cells in DEP buffer (8.0% sucrose, 0.3% dextrose, 0.1% bovine serum albumin, and 1 mM Tris.HCl (pH 8.0)) in the parallel-channel design when no AC electric field was applied. The microchannels used here were 200 μm wide×25 μm tall×2.95 mm long.
Figure 10B:
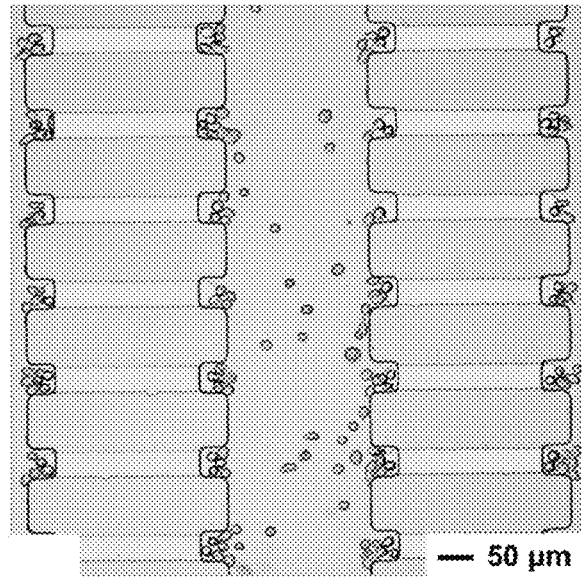
FIG. 10B shows MDA-MB-231 cells being trapped in the chambers of the parallel-channel design when an AC electric field was applied at 40 kHz.
Figure 10C:
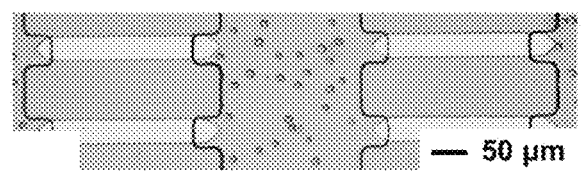
FIG. 10C shows the bright field image of the Jurkat E6-1 T-cells in DEP buffer (8.0% sucrose, 0.3% dextrose, 0.1% bovine serum albumin, and 1 mM Tris.HCl (pH 8.0)) in the parallel-channel design when no AC electric field was applied.
Figure 10D:
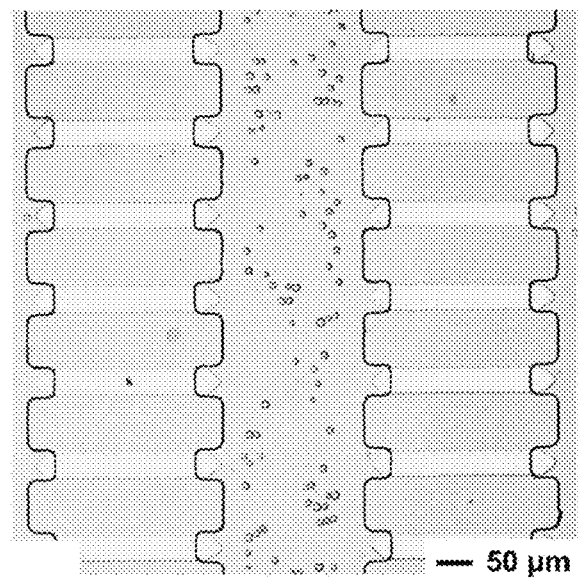
FIG. 10D shows Jurkat E6-1 T cells positions in the parallel-channel design when an AC electric field was applied at 40 kHz.

The separation performance of the parallel-channel design was studied using Jurkat E6-1 T and MDA-MB-231 as model white blood cells (WBCs) and CTCs, respectively. The bright field images of the individual cell types in the parallel-channel design is shown in FIG. 10A, FIG. 10B, FIG. 10C, and FIG. 10D. FIG. 10A shows the bright field image of the MDA cells in DEP buffer (8.0% sucrose, 0.3% dextrose, 0.1% bovine serum albumin, and 1 mM Tris.HCl (pH 8.0)) in the parallel-channel design when no AC electric field was applied. The microchannels used here were 200 µm wide×25 µm tall×2.95 mm long. FIG. 10C shows the bright field image of the Jurkat E6-1 T cells in DEP buffer (8.0% sucrose, 0.3% dextrose, 0.1% bovine serum albumin, and 1 mM Tris.HCl (pH 8.0)) in the parallel-channel design when no AC electric field was applied. When no electric field was applied, the cells flowed freely through the microchannels (50 μm/s) as shown in FIG. 10A and FIG. 10C. When an AC electric field was applied at 40 kHz, MDA cells were trapped in the chambers as shown in FIG. 10B, while Jurkat cells remained flowing and formed "pearl chains" in the microchannels as shown in FIG. 10D. The clear discrimination of the DEP responses for the two types of cells at 40 kHz indicated that the frequency was sufficient for separation.

Example 9

Evaluation of BPE Array Device in Open-Channel Design for Cell Separation

Figure 11A:
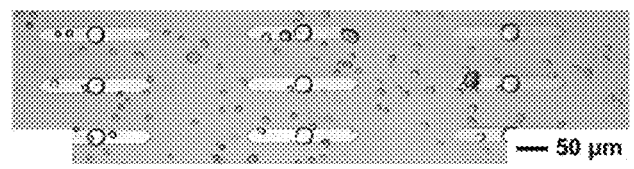
FIG. 11A shows a bright field image of the MDA-MB-231 cells flowing through the open-channel device when no AC field is applied. The microchannels used here were 200 μm wide×25 μm tall×2.65 mm long.
Figure 11B:
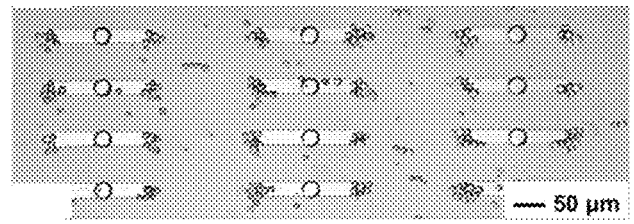
FIG. 11B shows a bright field image of the MDA-MB-231 cells at the channel junction (insulating wall between two adjacent channels) with 86.7 Vrms at 40 kHz.
Figure 11C:
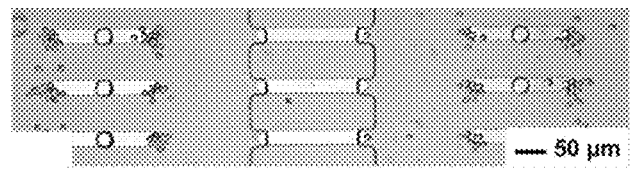
FIG. 11C shows a bright field image of the MDA-MB-231 cells in a channel with 86.7 Vrms at 40 kHz.

DEP responses for the two model cell lines in the open-channel design are shown in FIG. 11A, FIG. 11B, FIG. 11C, FIG. 11D, FIG. 11E, and FIG. 11F. The microchannels used here were 200 μm wide×25 μm tall×2.65 mm long. The response of the MDA cells is shown in FIG. 11A-FIG. 11C. FIG. 11A shows a bright field image of the MDA-MB-231 cells flowing through the open-channel device when no AC field was applied. FIG. 11B shows a bright field image of the MDA-MB-231 cells at the channel junction (insulating wall between two adjacent channels) with 86.7 Vrms at 40 kHz. FIG. 11C shows a bright field image of the MDA-MB-231 cells in a channel with 86.7 Vrms at 40 kHz. The MDA cells exhibited a pDEP response in the presence of the field and were trapped at the BPE tips. Less trapping was observed near the inter-microchannel junctions despite the stronger electric field anticipated there because less MDA cells flowed near to the junction.

Figure 11D:
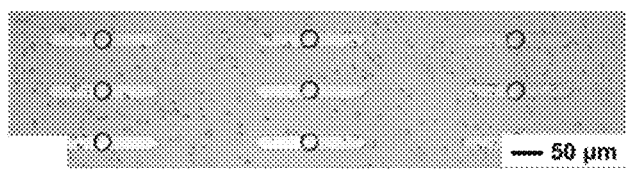
FIG. 11D shows a bright field image of the Jurkat E6-1 T cells flowing through the open-channel device when no AC field is applied.
Figure 11E:
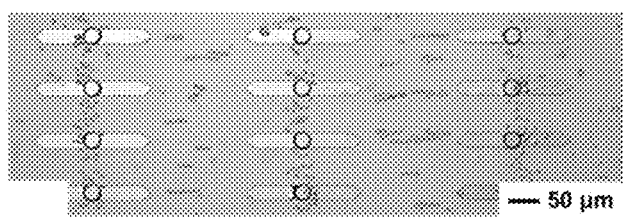
FIG. 11E shows a bright field image of the Jurkat E6-1 T cells at the channel junction of the open-channel design with 157 Vrms at 40 kHz.
Figure 11F:
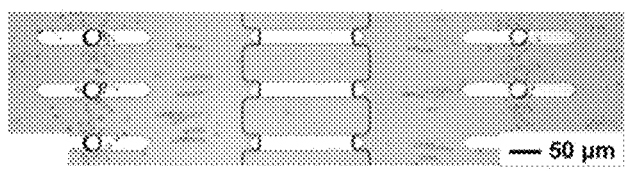
FIG. 11F shows a bright field image of the Jurkat E6-1 T cells in a channel of the open-channel design with 157 Vrms at 40 kHz.

Likewise, FIG. 11D shows a bright field image of the Jurkat E6-1 T cells flowing through the open-channel device when no AC field was applied. FIG. 11E shows a bright field image of the Jurkat E6-1 T cells at the channel junction of the open-channel design with 157 Vrms at 40 kHz. FIG. 11F shows a bright field image of the Jurkat E6-1 T cells in a channel of the open-channel design with 157 Vrms at 40 kHz. Notably, when the Jurkat cells undergo nDEP, they were repelled to either two regions of the microchannels with a low electric field—directly above the center line of the BPEs or along the midline between BPEs. This feature is favorable for separation of CTCs from blood because it provides more paths for the large number of WBCs in blood samples to pass through.

Example 10

Selective Capture of Cancer Cells by a BPE Device in Parallel-Channel Design

MDA-MB-231 cells and Jurkat E6-1 T cells were labeled with Alexa Fluor® 488 anti-human EGFR Antibody and PE anti-human CD45 Antibody (Biolegend; San Diego, Calif.), respectively. For labeling, 5 μL antibody was added to 100 μL buffer (PBS with 10% FBS) containing a million cells. The detailed labeling procedure was as follows. First, the labeling solution was vortexed for 1 min to disperse antibodies and to break up aggregates. 5 μL of this solution was subsequently diluted in cell labeling buffer (total volume 100 μL). Second, the mixture was centrifuged at 15,000×g (4° C.) and 5 μL at the bottom (containing aggregates) was discarded. The cell pellets were washed with PBS buffer before and then adding into this labeling mixture. Third, the pellets were mixed well with the labeling mixture on a rocker at room temperature for 1 hour. Finally, the cells were washed with DEP buffer several times and resuspended at a concentration of $1\times10^6$ cells/mL. Pre-stained MDA cells were then spiked into Jurkat E6-1 T cells for subsequent separation experiments. To determine the mean spiking count, 5 μL of the mixed cell solution were pipetted on a microscope slide and manually counted in triplicate.

After coating with Pluronic, all microchannels were rinsed with DEP buffer for 15 min before adding cells into the microfluidic devices. The AC electric field was applied to the gold driving electrodes at each side of the BPE arrays using a Tektronix AFG3011C waveform generator (Tektronix, Beaverton, Oreg.) and Trek model 2205 amplifier (Trek, Lockport, N.Y.). The distance between two driving electrodes were 15.266 mm. For the trapping experiments, the AC applied was 245 Vpp (86.7 Vrms). Therefore, the electric field was 16.05 KV/m. The AC frequency was maintained at 40 kHz at which MDA-MB-231 cells experienced strong pDEP, while Jurkat E6-1 T cells exhibited nDEP. Nikon eclipse Ti inverted microscope and Nikon AZ-100 microscope (Nikon, Tokyo, Japan) were utilized to image cells with fluorescent labeling and cells on the top of BPEs, respectively.

MDA-MB-231 cells and Jurkat E6-1 T cells were labeled with Alexa Fluor® 488 anti-human EGFR antibody and phycoerythrin (PE) anti-human CD45 antibody (BioLegend; San Diego, Calif.), respectively. Briefly, 5.0 μL of the appropriate antibody solution was diluted to 100 μL in cell labeling buffer (1×PBS with 10% FBS) to label one million cells. The detailed labeling procedure was as follows. First, the antibody solution was vortexed for 1 min to disperse antibodies and to break up aggregates. 5.0 μL of this solution was subsequently diluted in cell labeling buffer (to 100 μL). Second, the mixture was centrifuged at 15,000×g (4.0° C., 10 min) and 5.0 μL at the bottom (containing aggregates) was discarded. The cell pellets were washed with 1×PBS buffer before suspending at $1.0\times10^6$ cells/100 μL in this labeling mixture. Third, the cells in labeling mixture were kept on a rocker at room temperature for 1 hour. Finally, the cells were washed with DEP buffer twice and resuspended at a concentration of $1.0\times10^6$ cells/mL. Pre-stained MDA cells were then spiked into Jurkat E6-1 T cells for subsequent separation experiments. To determine the mean spiking count, 5.0 μL of the mixed cell solution were pipetted on a microscope slide and manually counted in triplicate.

Figure 12A:
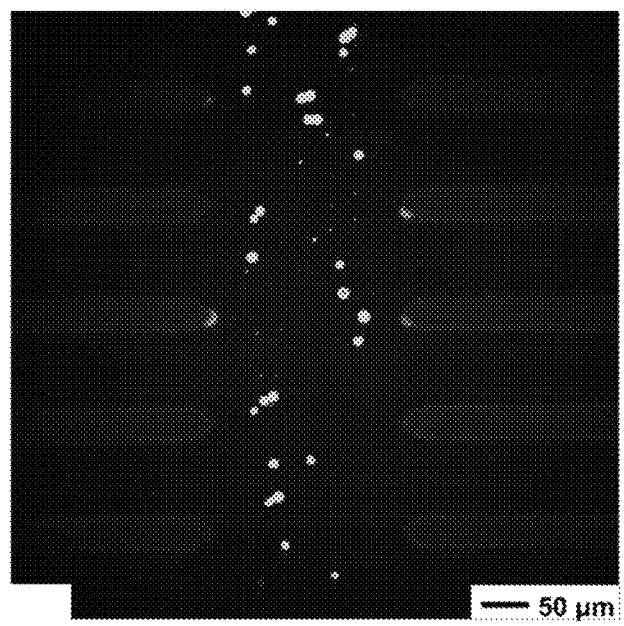
FIG. 12A shows an overlay of two fluorescence micrographs (yellow and green) showing the response of MDA-MB-231 cells and Jurkat cells to a 40 kHz AC electric field applied for a few minutes to the BPE array device in the parallel-channel design.
Figure 12B:
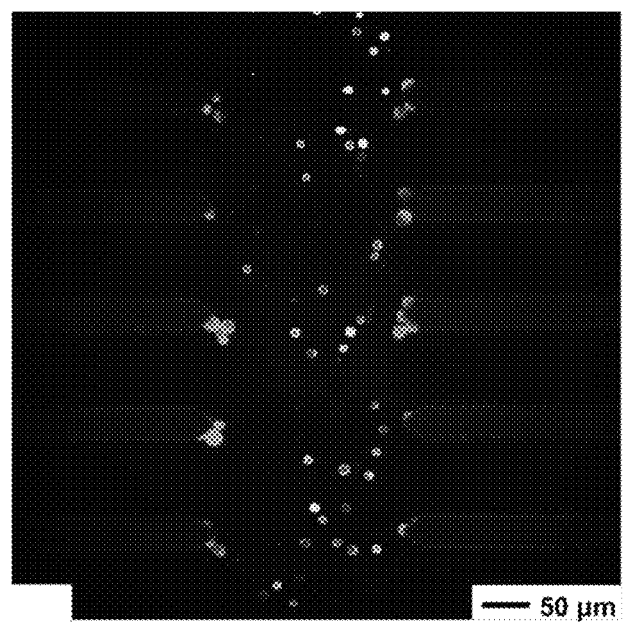
FIG. 12B shows an overlay of two fluorescence micrographs (yellow and green) showing the response of MDA-MB-231 cells and Jurkat cells to a 40 kHz AC electric field applied for a few minutes to the BPE array device in the parallel-channel design.

In this experiment, the dye-linked antibody labeled cells were combined in DEP buffer to a final concentration of $5.0\times10^5$ MDA cells/mL and $1.0\times10^5$ Jurkat cells/mL and $1.0\times10^6$ MDA cells/mL and $1.0\times10^5$ Jurkat cells/mL, respectively. These concentrations were chosen to allow ample opportunity to observe MDA cell trapping. The mixed cell sample was flowed into the device at a rate of 60 μm/s and a 40 kHz AC field was applied. After allowing the MDA cells to be trapped at the BPE tips for 3 min, fluorescence images for each dye (Alexa 488/green and phycoerythrin/yellow) were taken in rapid sequence and overlayed to obtain the fluorescence micrograph images. FIG. 12A and FIG. 12B are the fluorescence micrographs that show the selective capture of model breast cancer cells from a mixture of both MDA (green) and Jurkat cells (yellow). These results are significant because they demonstrated the selective capture of breast cancer cells at low or high concentration from white blood cells in a high-throughput DEP microfluidic device at an array of wireless electrodes.

Example 11

Figure 13:
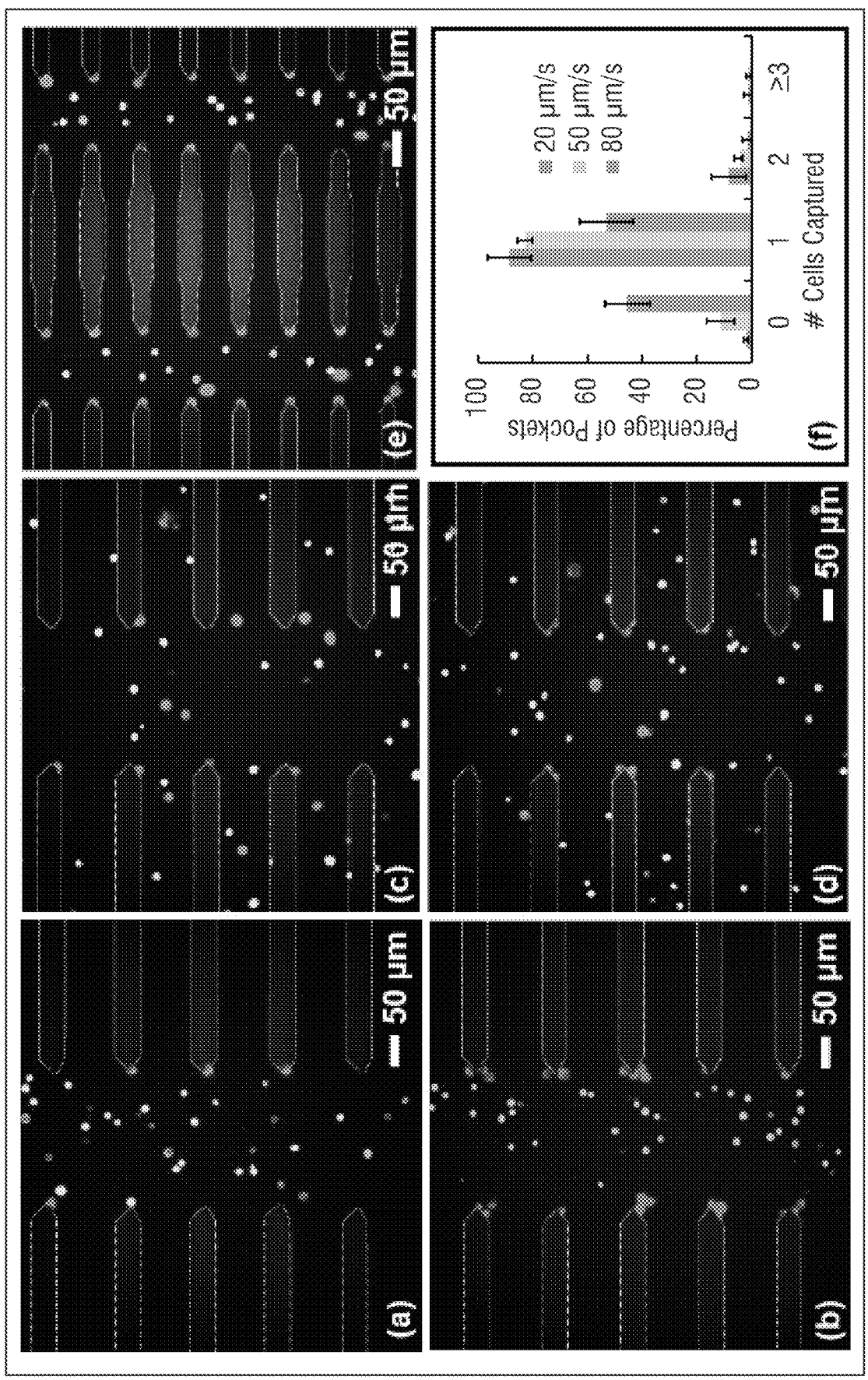
FIG. 13 demonstrates the capability of selective capture in both designs, and single-cell capture in a parallel-channel device with decreased pocket size. In all the fluorescent micrographs, 40 kHz AC electric field was applied to a mixture of the two cell types (MDA-MB-231 (green) and Jurkat (yellow)), in which MDA-MB-231 cells were labeled with Alexa Fluor® 488 anti-human EGFR antibody, and Jurkat cells were labeled with PE anti-human CD45 antibody. The response was recorded after the AC voltage was applied for 1 min (a), and for 3 min (b) in the parallel-channel design and for 1 min (c) and 3 min (d) in the open-channel design. (e) Fluorescent micrograph showing the capture of single MDA-MB-231 cells (green) after 3 min of AC field application in the modified parallel-channel design. (f) A plot of the single-cell capture performance at three average linear flow velocities (n=3).

Demonstration of Single-Cell Capture by Geometric Constraint in the Parallel-Channel Device To test the ability of the parallel-channel device to achieve single-cell capture by geometric constraint, we decreased the micropocket (microchamber) size from 40 µm long×40 µm wide to 30 µm long×25 µm wide. Pearl-chaining of cells can occur when there is insufficient drag force competing with the DEP capture force, and therefore, selective single-cell capture of MDA-MB-231 cells from Jurkat E6-1 T cells was evaluated under various flow rates or linear flow velocities. After MDA cells were captured under each flow velocity for approximately 5 min, images were taken and the number of MDA cells at each microchamber along 4 parallel microchannels was counted and averaged. According to the results shown in FIG. 13, it can be concluded that: (i) The present microfluidic device was robust in selectively isolating single cells under various flow velocities. (ii) Over 80% of microchambers obtained individual MDA cells when the flow velocity was less than 50 µm/s. Increasing the flow velocity beyond 50 µm/s decreased the likelihood of trapping multiple cells per microchamber; (iii) Regardless of flow rate or velocity, multi-cell capture was rare (<2%) using the current design. A key point is that the single-cell capture rate was far better than can be achieved by randomly partitioning the sample, for which Poisson statistics predicts that when 37% of micropockets contain a single cell, there will also be 37% empty, 18% with double occupancy and 7% containing three or more. Further, our design left open the option to capture cells under a slow flow velocity and to subsequently disrupt multiple occupancies by increasing the flow velocity. It is worth mention that the 10 µm gap between the BPE tip and the microchamber opening played a crucial role in capturing and stabilizing single cells. The strategy demonstrated here not only met the challenge of high-throughput and selective CTC isolation by DEP, but also enables single-cell capture.

Using the open-channel design, over 0.2 mL/h throughput can be achieved with a 39.6 mm$^2$ device footprint. If a larger device footprint were employed, as was the case for a 7500 mm$^2$ DEP device previously, a throughput of 18.9 mL/h could be achieved.

Even if the device were scaled to 2.21×10$^3$ mm$^2$, the footprint of a ApoStream device reported, the throughput would still be over 5.5 mL/h. In this scenario, 1.0 mL of blood could be processed in approximately 11 min. In addition, assuming 1-100 CTCs/mL of whole blood, the present parallel-channel device can process the standard volume (7.5 mL) employed in a commercial CellSearch system, without exhausting the 1408 capture sites (in the 40 mm$^2$ device). If a buffy coat from 1.0 mL of blood suspended to 100 µL DEP buffer is utilized, a ten-fold decrease in separation time can be expected.

Example 12

Demonstration of the Effect of BPE Spacing and Length

To test the capability of a microfluidic device with different BPEs and more specifically the effects of the length and spacing of BPEs in the same microfluidic device, a microfluidic device with the BPEs with different lengths and spacing was designed and tested with its capability to capture cells.

Figure 14A:
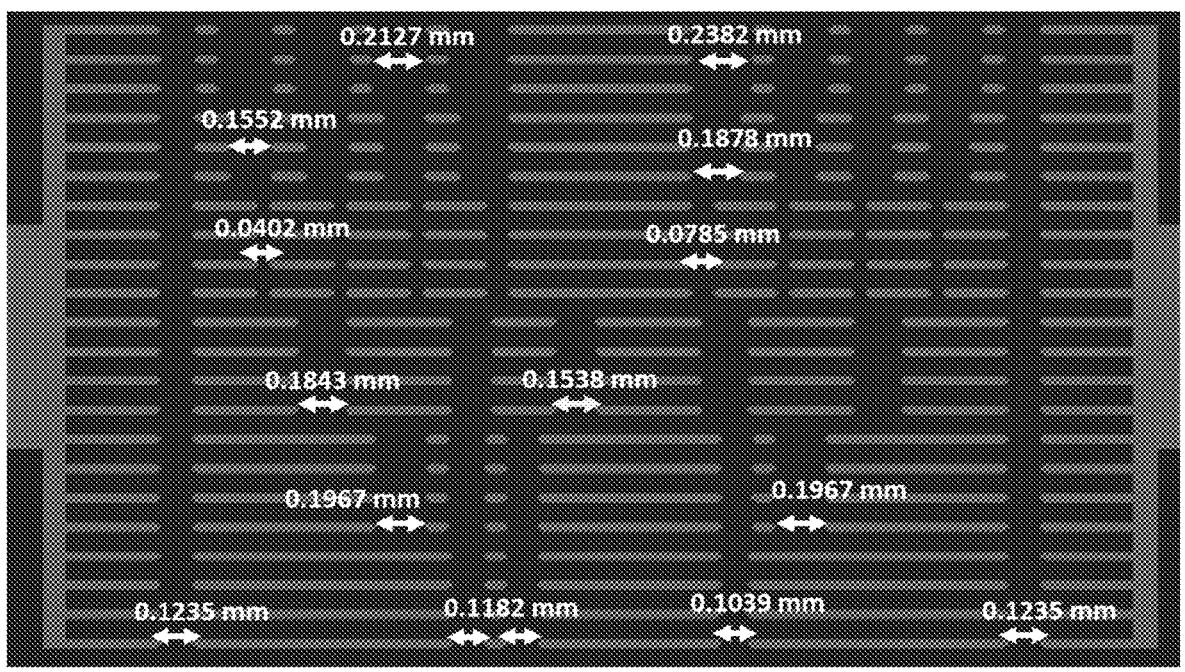
FIG. 14A shows a schematic for an open-channel microfluidic device with BPEs of different length and uniform spacing.
Figure 14B:
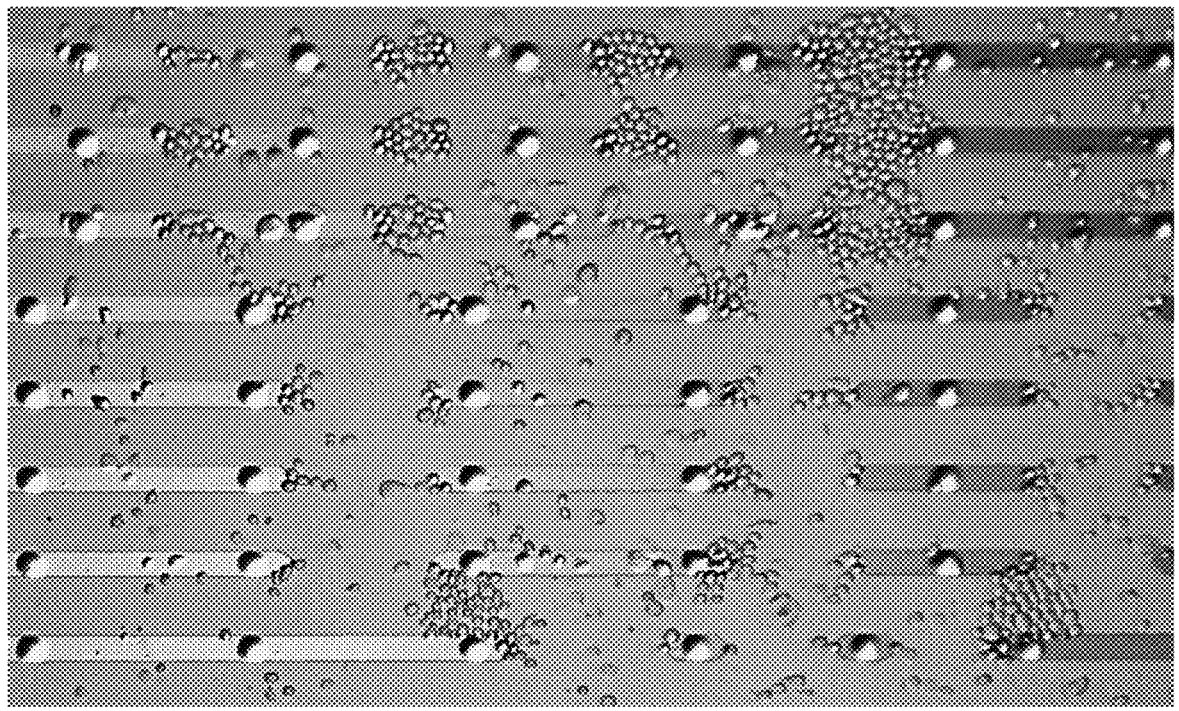
FIG. 14B shows a fluorescent micrograph of the capture of MDA cells after applying an AC of 100 Vpp and 70 kHz.

FIG. 14A shows a schematic for an open-channel microfluidic device with BPEs of different length, different BPE spacing and uniform microchannel spacing and FIG. 14B shows a fluorescent micrograph of the capture of MDA cells after applying an AC of 100 Vpp and 70 kHz. For this experiment, the MDA had a cell concentration of 4×10$^6$ cells per milliliter. The DEP buffer solution contained 8.0% sucrose, 0.3% dextrose, and 0.1% BSA in 1.0 mM Tris buffer (pH 8.1). The DEP buffer had a conductivity of 86.94 mS/cm and the flow rate or velocity was about 20 µm/s. This experiment shows that the length of BPEs has a dramatic effect on the number of cells captured at each tip. The inter-BPE spacing was also found to have a similar and dramatic effect.

While this invention may be embodied in many different forms, the described scientific papers and other referenced materials mentioned herein are incorporated by reference in their entirety. Furthermore, the invention encompasses any possible combination of some or all of the various embodiments mentioned herein, described herein and/or incorporated herein. In addition, the invention encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the following claims where the term "comprising" means "including, but not limited to". Those familiar with the art may recognize other equivalents to the specific embodiments described herein which equivalents are also intended to be encompassed by the following claims.

What is claimed is:

1. A microfluidic device comprising:
   one or more fluidic microchannels that are configured to retain and move an ionically conductive solution;
   one or more arrays of wireless bipolar electrodes; and
   a power source in electrical communication with the ionically conductive solution to supply an AC electric field to the ionically conductive solution;
   wherein each array of wireless bipolar electrodes comprises two or more bipolar electrodes;
   wherein the one or more arrays are placed along the one or more fluidic microchannels;
   wherein within any one of the arrays, any one of the wireless bipolar electrodes is connected via the ionically conductive solution with at least one other wireless bipolar electrode;
   wherein the microfluidic device comprises 2, 4, 8, 16, 32, 64, 128 or 256 fluidic microchannels; and
   wherein an AC field is applied to the device and faradaic reactions do not occur.

2. The microfluidic device of claim 1, wherein the one or more fluidic microchannels have a width of about 5 µm to about 200 µm, a depth of about 5 µm to about 100 µm, and a length of about 0.1 mm to about 10 mm.

3. The microfluidic device of claim 1, the one or more fluidic microchannels have two or more side walls, one or more bottom walls, one or more top walls, one or more circular walls, or a combination thereof.

4. The microfluidic device of claim 3, wherein the one or more arrays of wireless bipolar electrodes are placed along the bottom wall(s) of or inside the one or more fluidic microchannels.

5. The microfluidic device of claim 1, wherein the one or more fluidic microchannels are rectangular shaped fluidic microchannels and have two side walls and one bottom wall.

6. The microfluidic device of claim 1, wherein each of one or more fluidic microchannels is separated from another adjacent microchannel by a distance from about 50 μm to about 500 μm.

7. The microfluidic device of claim 1, wherein two or more microchannels are grouped together by fluidic connection at their respective end and then connect to another group of microchannels.

8. The microfluidic device of claim 1, wherein two or more microchannels are merged together into a bigger channel or reservoir.

9. The microfluidic device of claim 1, wherein the microfluidic device further comprises multiple fluidic microchambers, wherein the bipolar electrodes have one or two ends of the bipolar electrodes placed inside the fluidic microchamber or two microchambers, respectively, and wherein each bipolar electrode has either a rounded tip or a triangular end at one or two of its ends.

10. The microfluidic device of claim 9, wherein the fluidic microchambers resides inside side, bottom, top, circular wall(s), or a combination thereof of the one or more fluidic microchannels.

11. The microfluidic device of claim 9, wherein the fluidic microchamber has an opening to the one or more fluidic microchannels.

12. The microfluidic device of claim 9, wherein the fluidic microchamber has a width of from about 1 μm to about 200 μm, a height of from about 10 μm to about 100 μm, and a depth of from about 5 μm to about 50 μm, measured from the bottom of the microchamber to the edge of the fluidic microchannel.

13. The microfluidic device of claim 1, wherein some of the bipolar electrodes have their two ends in two different fluidic microchannels.

14. The microfluidic device of claim 1, wherein some of the bipolar electrodes have their two ends in the same fluidic microchannel.

15. The microfluidic device of claim 1, wherein one wireless bipolar electrode is away from its adjacent wireless bipolar electrode in the same array by a distance from about 5 μm to about 500 μm, measured from one edge of one wireless bipolar electrode to the closest edge of the adjacent electrode.

16. The microfluidic device of claim 1, wherein one array of wireless bipolar electrode is away from its adjacent array of wireless bipolar electrode by a distance of from about 20 μm to about 1,000 μm, measured from one end of an electrode in one array to its closest end of another electrode in the adjacent array.

17. The microfluidic device of claim 1, wherein the bipolar electrode has one or two triangular ends.

18. The microfluidic device of claim 1, wherein the bipolar electrode has a circular tip at one or two of its end.

19. The microfluidic device of claim 9, wherein the end of the bipolar electrodes is from about 5 μm to about 40 μm away from the edge of the closest fluidic microchannel or the openings of the microchambers in which the bipolar electrodes reside.

20. The fluidic device of claim 3, wherein the wall(s) of the fluidic microchannels comprises polydimethylsiloxane, polymethylmethacrylate (PMMA), a polymeric material, glass material, or a combination thereof.

21. The microfluidic device of claim 1, wherein the wireless bipolar electrode comprises an electric conductor or semiconductor.

22. The microfluidic device of claim 1, wherein the bipolar electrode has a width from about 1 μm to about 50 μm, a thickness from about 1 μm to about 50 μm, a length from about 10 μm to about 1,000 μm, or combination thereof.

23. The microfluidic device of claim 1, wherein the wireless bipolar electrodes in the same microchannel are parallel to each other.

24. A method of isolation of a cell from a biological matrix comprising:
  contacting a biological sample with an ionically conductive solution in a fluidic device of claim 9, and
  applying an AC electric field to the ionically conductive solution for a period of time so a targeted cell is trapped at the tip of the bipolar electrode or aggregated at a point where the electric field is a local maximum;
  wherein the biological sample contains a targeted cell to be isolated;
  wherein the ionically conductive solution has a linear flow velocity from about 0.1 μm/s to about 80 μm/s;
  wherein the AC field is communicated across the wall of any one of the microchannels enabling simultaneous cell trapping across one or more microchannels; and
  wherein no DC electric field is applied to the device and faradaic reactions do not occur.

25. The method of claim 24, wherein the method further comprises washing the one or more fluidic microchannels with an ionically conductive solution.

26. The method of claim 24, wherein the method further comprises collecting the targeted cell.

27. The method of claim 24, wherein the targeted cell is a circulating tumor cell (CTC).

28. The method of claim 24, wherein the ionically conductive solution has a linear flow velocity from about 0.1 μm/s to about 80 μm/s.

29. The method of claim 24, wherein the biological matrix is a blood sample.

* * * * *